United States Patent
Liu

(10) Patent No.: US 7,304,074 B2
(45) Date of Patent: Dec. 4, 2007

(54) SUBSTITUTED 1,5-NAPHTHYRIDINE AZOLINONES

(75) Inventor: Jin-Jun Liu, Warren, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/368,936

(22) Filed: Mar. 6, 2006

(65) Prior Publication Data

US 2006/0223843 A1 Oct. 5, 2006

Related U.S. Application Data

(60) Provisional application No. 60/668,246, filed on Apr. 5, 2005.

(51) Int. Cl.
*C07D 471/02* (2006.01)
*A01N 43/42* (2006.01)
*A61K 31/44* (2006.01)

(52) U.S. Cl. .................... 514/300; 546/122

(58) Field of Classification Search ........... 546/122; 514/300

See application file for complete search history.

(56) References Cited

U.S. PATENT DOCUMENTS

2002/0165259 A1  11/2002  Rawlins et al.
2006/0084673 A1*  4/2006  Liu ........................... 514/300

FOREIGN PATENT DOCUMENTS

| WO | WO 96/14843 | 5/1996 |
|----|-------------|--------|
| WO | WO 97/34876 | 9/1997 |
| WO | WO 99/21845 | 5/1999 |
| WO | WO 02/20524 | 3/2002 |
| WO | WO 2004/006916 | 1/2004 |
| WO | WO 2004/007491 | 1/2004 |
| WO | WO 2004/026872 | 4/2004 |
| WO | WO 2004/047760 | 6/2004 |
| WO | WO 2005/011686 | 2/2005 |

OTHER PUBLICATIONS

Freshney et al., Culture of Animal Cells, A Manual of Basic Technique, Alan R. Liss, Inc., 1983, New York, p. 1-6.*
Dermer et al., Bio/Technology, 1994, 12:320.*
Nasmyth, K., Science, vol. 274, pp. 1643-1645 (1996).
Morgan, D. O., Ann. Rev. Cell Dev. Biol. vol. 13 pp. 261-291 (1997).
Kwon et al., J. Med. Chem. 1991, vol. 34, pp. 1845-1849.
Parast et al., Biochemistry, vol. 37, pp. 16788-16801 (1998).
Connell-Crowley et al., Cell Cycle: Materials and Methods (Michele Pagano, ed. Springer, Berlin, Germany) 1995, pp. 169-174.
Wermuth, C. G., Practice of Medicinal Chem. pp. 203-237 (1996).

* cited by examiner

*Primary Examiner*—Margaret D. Seaman
*Assistant Examiner*—Niloofar Rahmani
(74) *Attorney, Agent, or Firm*—George W. Johnston; Patricia S. Rocha-Tramaloni

(57) ABSTRACT

Substituted 1,5-naphthyridine azolinones inhibit Cdk1 and are selective against Cdk2 and Cdk4. These compounds and their pharmaceutically acceptable salts have antiproliferative activity and are useful as anti-cancer agents.

40 Claims, No Drawings

SUBSTITUTED 1,5-NAPHTHYRIDINE AZOLINONES

PRIORITY TO RELATED APPLICATIONS

This application claims the benefit of U.S. Provisional Application No. 60/668,246, filed Apr. 5, 2005, which is hereby incorporated by reference in its entirety.

FIELD OF THE INVENTION

The field of this invention relates to substituted 1,5-naphthyridine azolinones capable of inhibiting the activity of cyclin-dependent kinases, most particularly cyclin-dependent kinase 1 (Cdk1). Most preferably, the compounds of the invention inhibit Cdk1 and are selective against Cdk2 and Cdk4. These compounds and their pharmaceutically acceptable salts have antiproliferative activity and are useful, inter alia, in the treatment or control of cancer, in particular solid tumors. This invention also provides pharmaceutical compositions containing such compounds and the methods of treating or controlling cancer, most particularly the treatment or control of breast, lung, colon and prostate tumors.

BACKGROUND OF THE INVENTION

Cyclin-dependent kinases (Cdks) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science,* 274:1643-1677 (1996); and *Ann. Rev. Cell Dev. Biol.,* 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Because CDKs such as CDK1 serve as general activators of cell division, inhibitors of CDK1 can be used as antiproliferative agents. These inhibitors can be used for developing therapeutic intervention in suppressing deregulated cell cycle progression.

It is desirable to provide small molecule inhibitors of Cdk1 that are selective against other Cdks. That is, the small molecule is significantly more inhibitory of Cdk1 activity than Cdk2 and/or Cdk4 activity. Preferably, the compounds of the invention are at least two times, most preferably ten times, more inhibitory of Cdk1 activity than Cdk2 activity and at least five hundred times, preferably one thousand times, more inhibitory of Cdk1 activity than Cdk4 activity. Selectivity is believed to be a desirable parameter because of the potential concomitant toxicity and other undesirable complications that may follow from inhibiting multiple targets. Thus, for purposes of this invention, the inhibition of Cdk2 and Cdk4 are monitored to determine the selectivity of the inhibition of Cdk1. A compound that exhibits selectivity against Cdk2 and Cdk4 is expected to have a better safety profile than a compound that is not selective between Cdk1, Cdk2, and Cdk4.

SUMMARY OF THE INVENTION

One aspect of the invention is a compound of the formula:

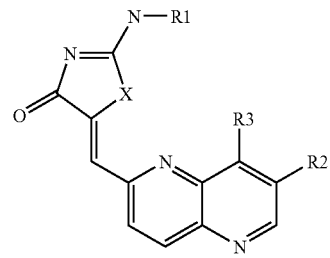

I wherein
  X is —S— or —NH—;
  $R^1$ is selected from the group consisting of
    a) hydrogen,
    b) lower alkyl that optionally may be substituted by
      (1) aryl that optionally may be substituted by lower alkyl, OH, lower alkoxy, halogen, or perfluoro-lower alkyl,
      (2) heteroaromatic that optionally may be substituted by lower alkyl, =O, and —NH, or
      (3) heterocyclo lower alkyl,
    c) cyclo lower alkyl that optionally may be substituted by aryl,
    d) lower alkoxy-lower alkyl, e)
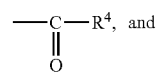
  f)

$R^2$ is selected from the group consisting of
    a) cyano,
    b) hydrogen,
    c) $CONR^6R^7$,
    d) $CO_2R^8$, and
    e) lower alkyl optionally substituted by
      (1) $OR^9$,
      (2) cyano, or
      (3) $NR^6R^7$;
  $R^3$ selected from the group consisting of
    a) O-lower alkyl,
    b) S-lower alkyl,
    c) hydrogen,
    d) lower alkyl, e) cyclo lower alkyl,
f) lower alkene,
g) lower alkylene,
h) NR$^6$R$^7$,
i) COOR$^8$, and
j) CONR$^6$R$^7$,
wherein, in each instance, lower alkyl, cyclo lower alkyl, lower alkene and lower alkylene may optionally be substituted by
(1) OR$^9$,
(2) cyano, and
(3) NR$^6$R$^7$,
R$^4$ is selected from the group consisting of
a) hydrogen,
b) lower alkyl,
c) O-lower alkyl,
d) Cyclo lower alkyl containing from 3 to 6 carbon atoms, and e)

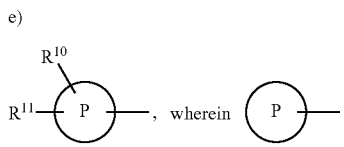

is selected from (1) an aryl ring, (2) a heterocyclo lower alkyl ring and (3) heteroaromatic ring;
R$^5$ is selected from the group consisting of hydrogen and lower alkyl;
R$^6$ and R$^7$ are each independently selected from the group consisting of
a) hydrogen,
b) lower alkyl which optionally may be substituted by
(1) OR$^9$,
(2) halogen,
(3) cyano, and
(4) NR$^{12}$NR$^{13}$, and
c) cyclo lower alkyl;
R$^8$ is selected from the group consisting of lower alkyl that optionally may be substituted by OR$^9$, cyano or NR$^6$R$^7$;
R$^9$ is selected from the group consisting of
a) hydrogen, and
b) lower alkyl that optionally may be substituted by
(1) OR$^{12}$,
(2) cyano, or
(3) NR$^6$R$^7$;
R$^{10}$ and R$^{11}$ are each independently selected from the group consisting of
a) hydroxy,
b) hydroxy-lower alkyl,
c) hydrogen,
d) lower alkyl,
e) halogen,
f) perfluro lower alkyl, and
g) lower alkoxy;
R$^{12}$ and R$^{13}$ are each independently selected from the group consisting of
a) hydrogen,
b) lower alkyl, and
c) cyclo lower alkyl; and
p is an integer from 0 to 6;

or a pharmaceutically acceptable salt thereof.

The compounds of the invention inhibit the activity of Cdks, particularly, Cdk1. Most preferably, the compounds of the invention inhibit Cdk1 and are selective against Cdk2 and Cdk4.

The invention is also directed to pharmaceutical compositions containing compounds of formula I, or a pharmaceutically acceptable salt thereof, and the use of the compounds and pharmaceutical compositions of the invention in the treatment various diseases and/or disorders associated with uncontrolled or unwanted cellular proliferation, such as cancer, autoimmune diseases, viral diseases, fungal diseases, neurodegenerative disorders and cardiovascular diseases. In particular, the compounds of the invention and pharmaceutical compositions containing such compounds are useful in the treatment of solid tumors, most particularly, breast, colon, lung and prostate tumors.

DETAILED DESCRIPTION OF THE INVENTION

Definitions

As used herein, the following terms have the following definitions:

"Aryl" means a monovalent mono- or bicyclic unsubstituted aromatic hydrocarbon ring, such as phenyl or naphthyl, with phenyl being preferred.

"Cyano" means the monovalent radical —CN.

"Cyclo lower alkyl" means a non-aromatic, partially or completely saturated, cyclic, monovalent, aliphatic hydrocarbon group containing 3 to 8 carbon atoms, preferably 4 to 6 carbon atoms. Examples of cyclo lower alkyl groups include cyclopropyl, cyclobutyl, cyclopentyl, cyclohexyl, etc., with cyclopropyl being especially preferred.

"Cyclo lower alkylene" designates a cyclo lower alkenyl substituent which is a divalent unsubstituted 3 to 6 membered saturated carbocyclic hydrocarbon ring. Among the preferred cyclo lower alkylene substituents are cyclopropenyl and cyclobutenyl.

"Effective amount" or "Therapeutically Effective amount" is as defined in paragraph [0117] page 27.

"Halogen" means chlorine, fluorine, bromine and iodine, preferably chlorine and bromine.

"Hetero atom" means an atom selected from N, O and S.

"Heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are thiophenyl, thioazole, pyridinyl, furanyl, etc.

"Heterocyclo lower alkyl" refers to a 4 to 6 membered monocyclic saturated ring containing 3 to 5 carbon atoms and one or two hetero atoms selected from the group consisting of oxygen, nitrogen or sulfur. Among the preferred heterocyclic alkyl groups are mopholinyl, thiopyranyl or tetrahydro pyranyl.

"Hydroxy or Hydroxyl" means —OH.

"Hydroxy-lower alkyl" means a lower alkyl group, as defined above, which is substituted, preferably monosubstituted, by a hydroxy group.

"Ki" (inhibitory constant) refers to a measure of the thermodynamic binding of the ligand/inhibitor (that is, a compound according to the invention) to the target protein. K$_i$ can be measured, inter alia, as is described in Example 28, infra.

"Lower alkene" means an unsaturated hydrocarbon which contains double bonds and has from one to six carbon atoms.

"Lower alkoxy" means a straight-chain or branched-chain alkoxy group formed from lower alkyl containing form one to six carbon atoms, such as methoxy, ethoxy, n-propoxy, isopropoxy, n-butoxy, tert-butoxy and the like.

"Lower alkoxy-lower alkyl" means a lower alkyl substituent as defined above which is substituted, preferably monosubstituted, with a lower alkoxy group, wherein lower alkoxy is as defined above.

"Lower alkoxy-lower alkylene" denotes a lower alkylene substituent, as designated hereinbefore, which is substituted, preferably it is monosubstituted, with a lower alkoxy group, where lower alkoxy is defined as above.

"Lower alkylene" designates a divalent saturated straight or branched-chain hydrocarbon substituent containing from one to six carbon atoms, such as ethylene-, propylene-.

"Lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

"Perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, with trifluoromethyl being especially preferred.

"Pharmaceutically acceptable salts" refers to conventional acid-addition salts or base-addition salts that retain the biological effectiveness and properties of the compounds of formula I and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

In an embodiment, the invention is directed to compounds of formula I

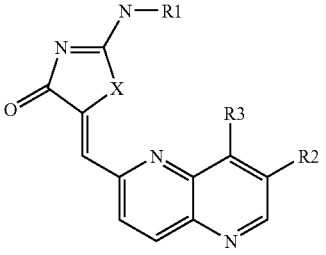

wherein $R^1$, $R^2$, $R^3$, and X are as defined above;

or a pharmaceutically acceptable salt thereof.

In a preferred embodiment, the invention is directed to compounds of formula I-A

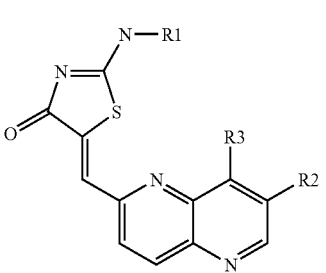

wherein $R^1$, $R^2$ and $R^3$ are as defined above; or a pharmaceutically acceptable salt thereof.

In an embodiment of formula I-A, $R^1$ is H.

In another embodiment of formula I-A, $R^1$ is lower alkyl that optionally may be substituted by
(1) aryl that optionally may be substituted by lower alkyl, OH, lower alkoxy, halogen, or perfluoro-lower alkyl,
(2) heteroaromatic that optionally may be substituted by lower alkyl, =O, and —NH, or
(3) heterocyclo lower alkyl.

In another embodiment of formula I-A, $R^1$ is cyclo lower alkyl that optionally may be substituted by aryl.

In another embodiment of formula I-A, $R^1$ is lower alkoxy-lower alkyl.

In another embodiment of formula I-A, $R^1$ is

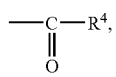

wherein $R^4$ is as defined above. Most preferably, $R^4$ is lower alkyl.

In another embodiment of formula I-A, $R^1$ is

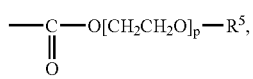

Wherein $R^5$ and p are as defined above. Most preferably $R^5$ is hydrogen and p is 1-2.

In another embodiment of formula I-A, $R^2$ is cyano.

In another embodiment of formula I-A, $R^2$ is hydrogen.

In another embodiment of formula I-A, $R^2$ is $CONR^6R^7$, wherein $R^6$ and $R^7$ are as defined above. Preferably, $R^6$ and $R^7$ are each independently H, lower alkyl, or lower alkyl substituted by $OR^9$. Most preferably, $R^9$ is hydrogen.

In another embodiment of formula I-A, $R^2$ is $CO_2R^8$, wherein $R^8$ is as defined above. Most preferably, $R^8$ is lower alkyl which optionally may be substituted by $OR^9$. Most preferably, $R^9$ is hydrogen or lower alkyl.

In another embodiment of formula I-A, $R^2$ is lower alkyl optionally substituted by $OR^9$, cyano, or $NR^6R^7$ wherein $R^6$, $R^7$ and $R^9$ are as defined above. Most preferably $R^6$ is hydrogen or lower alkyl, $R^7$ is hydrogen or lower alkyl and $R^9$ is hydrogen or lower alkyl.

In another embodiment of formula I-A, $R^3$ is O-lower alkyl, wherein the lower alkyl may be substituted as defined above in the definition of $R^3$, most preferably the lower alkyl is substituted by $OR^9$, wherein $R^9$ is as defined above.

In another embodiment of formula I-A, $R^3$ is S-lower alkyl, wherein the lower alkyl may be substituted as defined above in the definition of $R^3$, most preferably the lower alkyl is substituted by $OR^9$, wherein $R^9$ is as defined above.

In another embodiment of formula I-A, $R^3$ is hydrogen.

In another embodiment of formula I-A, $R^3$ is lower alkyl, wherein the lower alkyl may be substituted as defined above in the definition of $R^3$, most preferably the lower alkyl is substituted by $OR^9$, wherein $R^9$ is as defined above.

In another embodiment of formula I-A, $R^3$ is cyclo lower alkyl, wherein the lower alkyl may be substituted as defined above in the definition of $R^3$, most preferably the lower alkyl is substituted by $OR^9$, wherein $R^9$ is as defined above.

In another embodiment of formula I-A, $R^3$ is lower alkene, wherein the lower alkene may be substituted as defined above in the definition of $R^3$, most preferably the lower alkene is substituted by $OR^9$, wherein $R^9$ is as defined above.

In another embodiment of formula I-A, $R^3$ is lower alkylene, wherein the lower alkylene may be substituted as defined above in the definition of $R^3$, most preferably the lower alkylene is substituted by $OR^9$, wherein $R^9$ is as defined above.

In another embodiment of formula I-A, $R^3$ is $NR^6R^7$, wherein $R^6$ and $R^7$ are as defined above, most preferably $R^6$ and $R^7$ are each independently hydrogen or lower alkyl that optionally is substituted by $OR^9$, halogen or cyano, and wherein $R^9$ is as defined above.

In another embodiment of formula I-A, $R^3$ is $COOR^8$ wherein $R^8$ is as defined above. Most preferably $R^8$ is lower alkyl that is substituted by $OR^9$, wherein $R^9$ is as defined above.

In another embodiment of formula I-A, $R^3$ is $CONR^6R^7$, wherein $R^6$ and $R^7$ are as defined above, most preferably $R^6$ and $R^7$ are each independently hydrogen or lower alkyl that optionally is substituted by $OR^9$, halogen or cyano, and wherein $R^9$ is as defined above.

In a preferred embodiment of formula I-A $R^1$ is lower alkyl substituted by aryl that is substituted by halogen and/or lower alkyl.

In another preferred embodiment of formula I-A $R^1$ is lower alkyl substituted by heterocyclo lower alkyl.

In another preferred embodiment of formula I-A $R^1$ is cyclo lower alkyl that optionally may be substituted by aryl.

In another preferred embodiment of formula I-A $R^2$ is cyano.

In another preferred embodiment of formula I-! $R^2$ is hydrogen.

In another preferred embodiment of formula I-A $R^3$ is O-lower alkyl, preferably O-isopropyl.

In another preferred embodiment of formula I-A $R^3$ is hydrogen.

Examples of compounds of formula I-A include:

6-(2-Amino-4-oxo-4H-thiazol-5-ylidenemethyl)-4-isopropoxy-[1,5]naphthyridine-3-carbonitrile (Example 1);

6-[2-(2-Chloro-benzylamino)-5-oxo-3,5-dihydro-imidazol-4-ylidenemethyl]-4-isopropoxy-[1,5]naphthyridine-3-carbonitrile (Example 2);

4-Isopropoxy-6-[4-oxo-2-(2-phenyl-cyclopropylamino)-4H-thiazol-5-ylidenemethyl]-[1,5]naphthyridine-3-carbonitrile (Example 3);

4-Isopropoxy-6-{4-oxo-2-[(thiophen-2-ylmethyl)-amino]-4H-thiazol-5-ylidenemethyl}-[1,5]naphthyridine-3-carbonitrile (Example 4);

4-Isopropoxy-6-{2-[(3-methyl-thiophen-2-ylmethyl)-amino]-4-oxo-4H-thiazol-5-ylidenemethyl}-[1,5]naphthyridine-3-carbonitrile (Example 5);

6-[2-(2-Chloro-6-methyl-benzylamino)-4-oxo-4H-thiazol-5-ylidenemethyl]-4-isopropoxy-[1,5]naphthyridine-3-carbonitrile (Example 6);

6-{2-[2-(3-Fluoro-phenyl)-ethylamino]-4-oxo-4H-thiazol-5-ylidenemethyl}-4-isopropoxy-[1,5]naphthyridine-3-carbonitrile (Example 7);

6-[2-(2-Chloro-4-fluoro-benzylamino)-4-oxo-4H-thiazol-5-ylidenemethyl]-4-isopropoxy-[1,5]naphthyridine-3-carbonitrile (Example 8);

6-{4-Oxo-2-[(thiophen-2-ylmethyl)-amino]-4H-thiazol-5-ylidenemethyl}-[1,5]naphthyridine-3-carbonitrile (Example 11);

6-[4-oxo-2-(2-phenyl-cyclopropylamino)-4H-thiazol-5-ylidenemethyl]-[1,5]naphthyridine-3-carbonitrile (Example 12);

6-{2-[(3-Methyl-thiophen-2-ylmethyl)-amino]-4-oxo-4H-thiazol-5-ylidenemethyl}-[1,5]naphthyridine-3-carbonitrile (Example 13);

6-(2-Amino-4-oxo-4H-thiazol-5-ylidenemethyl)-[1,5]naphthyridine-3-carbonitrile (Example 14);

6-{2-[2-(3-fluoro-phenyl)-ethylamino]-4-oxo-4H-thiazol-5-ylidenemethyl}-[1,5]naphthyridine-3-carbonitrile (Example 15);

6-[2-(2-Chloro-benzylamino)-5-oxo-3,5-dihydro-imidazol-4-ylidenemethyl]-[1,5]naphthyridine-3-carbonitrile (Example 16);

6-[2-(2-Chloro-6-methyl-benzylamino)-4-oxo-4H-thiazol-5-ylidenemethyl]-[1,5]naphthyridine-3-carbonitrile (Example 17);

6-[2-(2-Chloro-4-fluoro-benzylamino)-4-oxo-4H-thiazol-5-ylidenemethyl]-[1,5]naphthyridine-3-carbonitrile (Example 18);

6-[2-(3-Chloro-4-fluoro-benzylamino)-4-oxo-4H-thiazol-5-ylidenemethyl]-[1,5]naphthyridine-3-carbonitrile (Example 19);

5-(8-Isopropoxy-[1,5]naphthyridin-2-ylmethylene)-2-(2-phenyl-cyclopropylamino)-thiazol-4-one (Example 20);

2-[2-(3-Fluoro-phenyl)-ethylamino]-5-(8-isopropoxy-[1,5]naphthyridin-2-ylmethylene)-thiazol-4-one (Example 21);

5-(8-Isopropoxy-[1,5]naphthyridin-2-ylmethylene)-2-[(thiophen-2-ylmethyl)-amino]-thiazol-4-one (Example 22);

2-(2-Chloro-benzylamino)-5-(8-isopropoxy-[1,5]naphthyridin-2-ylmethylene)-thiazol-4-one (Example 23);

2-(3-Chloro-4-fluoro-benzylamino)-5-(8-isopropoxy-[1,5]naphthyridin-2-ylmethylene)-thiazol-4-one (Example 24);

2-(2-Chloro-4-fluoro-benzylamino)-5-(8-isopropoxy-[1,5]naphthyridin-2-ylmethylene)-thiazol-4-one (Example 25);

[5-(8-Isopropoxy-[1,5]naphthyridin-2-ylmethylene)-4-oxo-4,5-dihydro-thiazol-2-yl]-carbamic acid tert-butyl ester (Example 26); and 2-Amino-5-(8-isopropoxy-[1,5]naphthyridin-2-ylmethylene)-thiazol-4-one (Example 27).

In another embodiment, the invention is directed to a compound of formula I-B

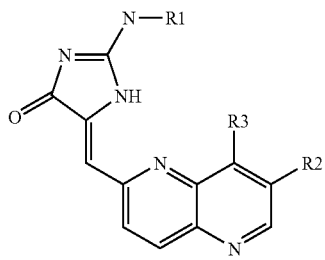

I-B wherein $R^1$, $R^2$ and $R^3$ are as defined above; or a pharmaceutically acceptable salt thereof.

In an embodiment of formula I-B, $R^1$ is H.

In another embodiment of formula I-B, $R^1$ is lower alkyl that optionally may be substituted by
(4) aryl that optionally may be substituted by lower alkyl, OH, lower alkoxy, halogen, or perfluoro-lower alkyl,
(5) heteroaromatic that optionally may be substituted by lower alkyl, =O, and —NH, or
(6) heterocyclo lower alkyl.

In another embodiment of formula I-B, $R^1$ is cyclo lower alkyl that optionally may be substituted by aryl.

In another embodiment of formula I-B, $R^1$ is lower alkoxy-lower alkyl.

In another embodiment of formula I-B, $R^1$ is

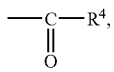

wherein $R^4$ is as defined above. Most preferably, $R^4$ is lower alkyl.

In another embodiment of formula I-B, $R^1$ is

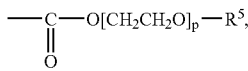

Wherein $R^5$ and p are as defined above. Most preferably $R^5$ is hydrogen and p is 1-2.

In another embodiment of formula I-B, $R^2$ is cyano.

In another embodiment of formula I-B, $R^2$ is hydrogen.

In another embodiment of formula I-B, $R^2$ is $CONR^6R^7$, wherein $R^6$ and $R^7$ are as defined above. Preferably, $R^6$ and $R^7$ are each independently H, lower alkyl, or lower alkyl substituted by $OR^9$. Most preferably, $R^9$ is hydrogen.

In another embodiment of formula I-B, $R^2$ is $CO_2R^8$, wherein $R^8$ is as defined above. Most preferably, $R^8$ is lower alkyl which optionally may be substituted by $OR^9$. Most preferably, $R^9$ is hydrogen or lower alkyl.

In another embodiment of formula I-B, $R^2$ is lower alkyl optionally substituted by $OR^9$, cyano, or $NR^6R^7$ wherein $R^6$, $R^7$ and $R^9$ are as defined above. Most preferably $R^6$ is hydrogen or lower alkyl, $R^7$ is hydrogen or lower alkyl and $R^9$ is hydrogen or lower alkyl.

In another embodiment of formula I-B, $R^3$ is O-lower alkyl, wherein the lower alkyl may be substituted as defined above in the definition of $R^3$, most preferably the lower alkyl is substituted by $OR^9$, wherein $R^9$ is as defined above.

In another embodiment of formula I-B, $R^3$ is S-lower alkyl, wherein the lower alkyl may be substituted as defined above in the definition of $R^3$, most preferably the lower alkyl is substituted by $OR^9$, wherein $R^9$ is as defined above.

In another embodiment of formula I-B, $R^3$ is hydrogen.

In another embodiment of formula I-B, $R^3$ is lower alkyl, wherein the lower alkyl may be substituted as defined above in the definition of $R^3$, most preferably the lower alkyl is substituted by $OR^9$, wherein $R^9$ is as defined above.

In another embodiment of formula I-B, $R^3$ is cyclo lower alkyl, wherein the lower alkyl may be substituted as defined above in the definition of $R^3$, most preferably the lower alkyl is substituted by $OR^9$, wherein $R^9$ is as defined above.

In another embodiment of formula I-B, $R^3$ is lower alkene, wherein the lower alkene may be substituted as defined above in the definition of $R^3$, most preferably the lower alkene is substituted by $OR^9$, wherein $R^9$ is as defined above.

In another embodiment of formula I-B, $R^3$ is lower alkylene, wherein the lower alkylene may be substituted as defined above in the definition of $R^3$, most preferably the lower alkylene is substituted by $OR^9$, wherein $R^9$ is as defined above.

In another embodiment of formula I-B, $R^3$ is $NR^6R^7$, wherein $R^6$ and $R^7$ are as defined above, most preferably $R^6$ and $R^7$ are each independently hydrogen or lower alkyl that optionally is substituted by $OR^9$, halogen or cyano, and wherein $R^9$ is as defined above.

In another embodiment of formula I-B, $R^3$ is $COOR^8$ wherein $R^8$ is as defined above. Most preferably $R^8$ is lower alkyl that is substituted by $OR^9$, wherein $R^9$ is as defined above.

In another embodiment of formula I-B, $R^3$ is $CONR^6R^7$, wherein $R^6$ and $R^7$ are as defined above, most preferably $R^6$ and $R^7$ are each independently hydrogen or lower alkyl that optionally is substituted by $OR^9$, halogen or cyano, and wherein $R^9$ is as defined above.

In a preferred embodiment of formula I-B $R^1$ is lower alkyl substituted by aryl that is substituted by halogen and/or lower alkyl.

In another preferred embodiment of formula I-B $R^1$ is lower alkyl substituted by heterocyclo lower alkyl.

In another preferred embodiment of formula I-B $R^1$ is cyclo lower alkyl that optionally may be substituted by aryl.

In another preferred embodiment of formula I-B $R^2$ is cyano.

In another preferred embodiment of formula I-B $R^2$ is hydrogen.

In another preferred embodiment of formula I-B $R^3$ is O-lower alkyl, preferably O-isopropyl.

In another preferred embodiment of formula I-B $R^3$ is hydrogen.

Examples of compounds of formula I-B include:
6-[2-(2,4-Bis-trifluoromethyl-benzylamino)-5-oxo-3,5-dihydro-imidazol-4-ylidenemethyl]-4-isopropoxy-[1,5]naphthyridine-3-carbonitrile, and
4-Isopropoxy-6-[5-oxo-2-(2-trifluoromethyl-benzylamino)-3,5-dihydro-imidazol-4-ylidenemethyl]-[1,5]naphthyridine-3-carbonitrile.

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

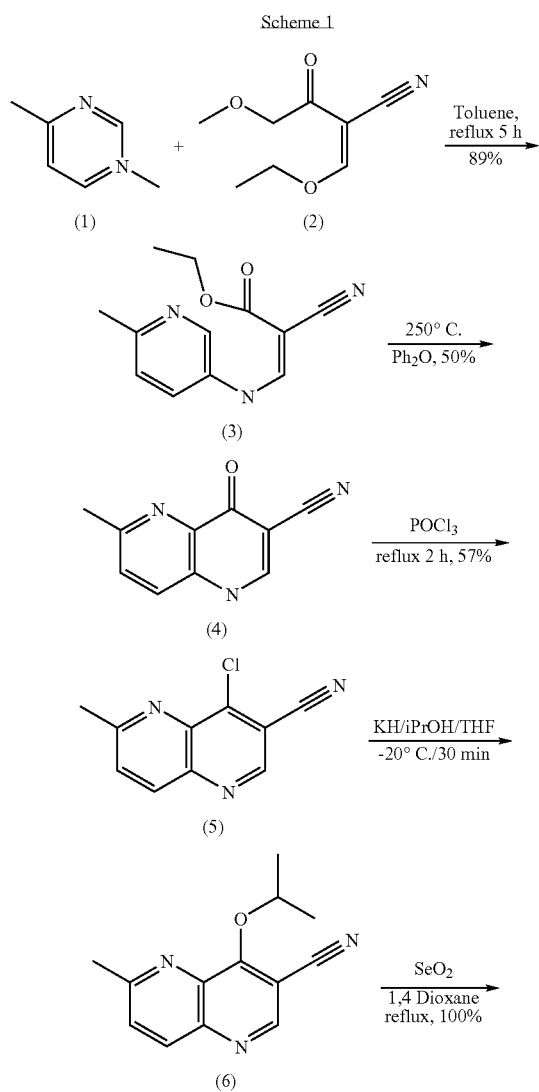

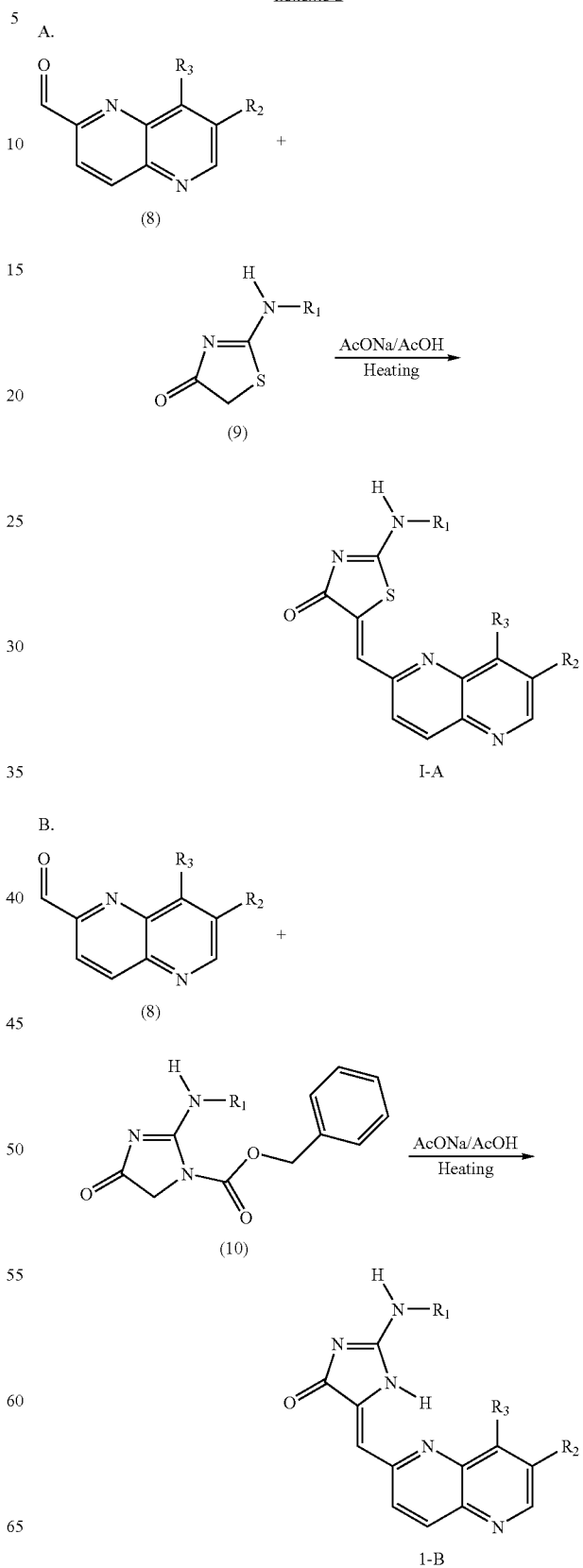

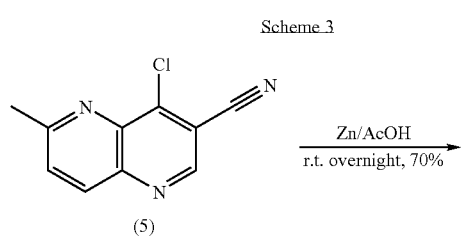
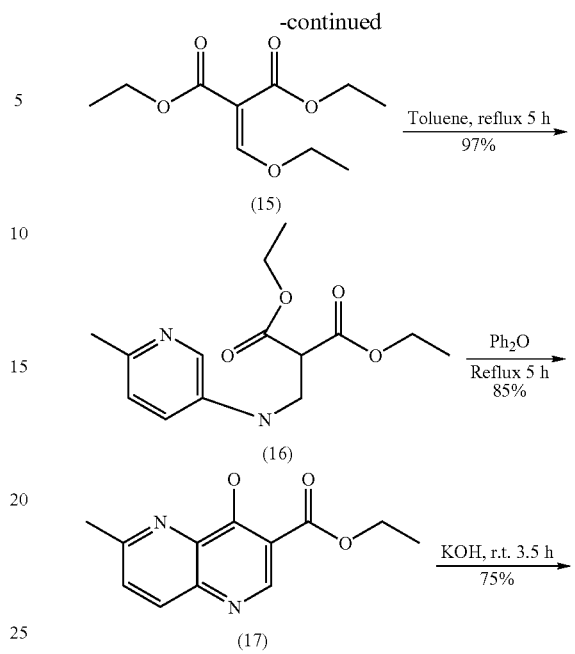
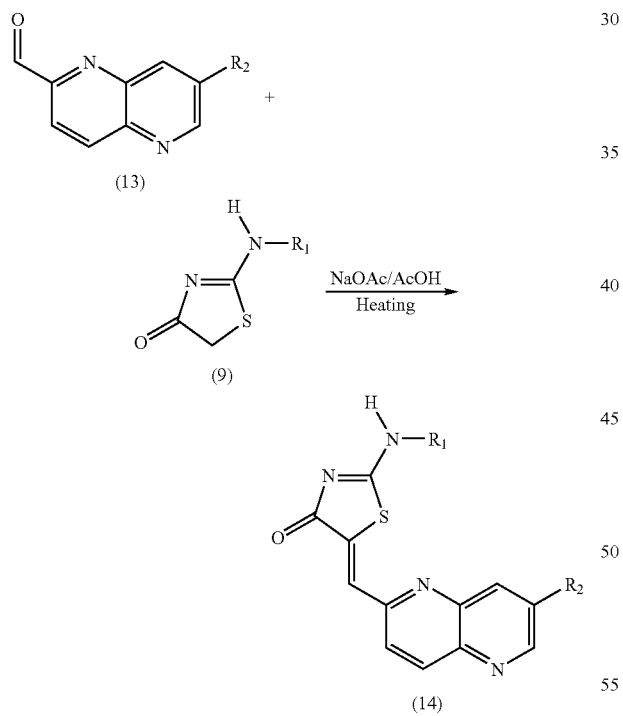

Scheme 6

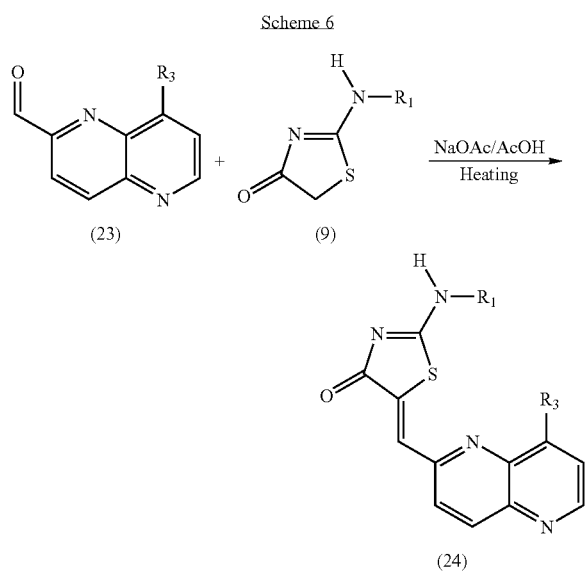

Compound 1 is commercially available from ChemPacific.

Compound 2 is commercially available from Aldrich.

Compound 8 may be prepared, for example, by the procedures described in scheme 1.

Compound 9 may be obtained as described in Example 5.

Compound 10 may be prepared, for example, by the procedures described in Kuon et al., J. Med. Chem, 1991, 34, 1845-1849.

Compound 13 may be prepared, for example, by the procedures described in schemes 2 and 3.

Compound 15 is commercially available from Fluka.

Compound 23 may be prepared, for example, by the procedures described in scheme 5.

Generally, the compounds of the invention may be prepared according to the synthetic schemes provided above. In addition, suitable processes for the preparation of these compounds are given in the examples.

Separating a Mixture of Stereoisomers into the Optically Pure Stereoisomers (when Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87-124).

Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I that Bears a Carboxylic Acid Group into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

Crystal Forms

When the compounds of the invention are solids, it is understood by those skilled in the art that these compounds, and their salts, may exist in different crystal or polymorphic forms, all of which are intended to be within the scope of the present invention and specified formulas.

Compositions/Formulations

In an alternative embodiment, the present invention includes pharmaceutical compositions comprising at least one compound of formula (I), or a pharmaceutically acceptable salt thereof and a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions. The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

To obtain a stable water-soluble dose form, a pharmaceutically acceptable salt of a compound of the invention can be dissolved in an aqueous solution of an organic or inorganic acid. If a soluble salt form is not available, the compound may be dissolved in a suitable cosolvent or combinations of cosolvents.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I).

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Dosages

As mentioned above, the compounds of the present invention, including the compounds of formula (I), are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention is further directed to methods of modulating or inhibiting protein kinase CDK1 activity, for example in mammalian tissue, by contacting with a compound of the invention. The activity of the compounds of the invention as anti-proliferative agents is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany) (1995); International Publication No. WO 97/34876; and International Publication No. WO 96/14843. These properties may be assessed, for example, by using one or more of the biological testing procedures set out in the examples below.

EXAMPLES

Example 1

6-(2-Amino-4-oxo-4H-thiazol-5-ylidenemethyl)-4-isopropoxy-[1,5]naphthyridine-3-carbonitrile

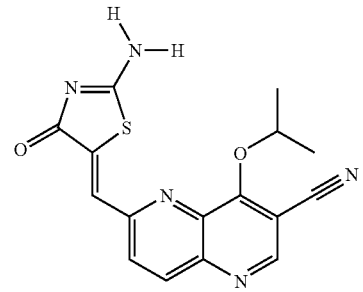

To a mixture of pseudothiohydantoin (Aldrich, 97%, 23.2 mg, 0.20 mmol), AcONa (160 mg, 1.95 mmol), molecular sieves, and 6-formyl-4-isopropoxy-[1,5]naphthyridine-3-carbonitrile (53.1 mg, 0.22 mmol) (prepared as described below) in a sealed tube was added AcOH (0.3 mL). The reaction mixture was heated to 85-95° C. for 1.5 h. The reaction mixture was then cooled to r.t. and triturated with water. The solid was collected by filtration and washed with water. The solid was then suspended in hot DMF (20 mL) and filtered again. The filtrate was concentrated to give a brown solid: 55.8 mg, which was then purified by Biotage flash column (1%-6% MeOH in $CH_2Cl_2$) to give 6-(2-amino-4-oxo-4H-thiazol-5-ylidenemethyl)-4-isopropoxy-[1,5]naphthyridine-3-carbonitrile as a yellowish solid (15.5 mg, 22.8%). HR-ES (+) m/e calcd for $C_{16}H_{13}N_5O_2S$ $(M+H)^+$ 340.0863. found 340.0863.

A. 6-Formyl-4-isopropoxyl-[1,5]Naphthyridine-3-carbonitrile

This compound was prepared as follows using the procedure of Scheme 1 above.

6-Formyl-4-isopropoxyl-[1,5]Naphthyridine-3-carbonitrile (7)

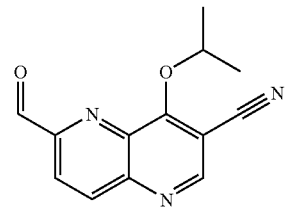

2-Cyano-3-(6-methyl-pyridin-3-ylamino)-acrylic acid ethyl ester (3): To a solution of 3-amino-6-picoline (ChemPacific, 15.00 g, 138.70 mmol), in toluene (400 mL) was added ethyl(ethoxymethylene)-cyano-acetate (Aldrich, 98%, 35.88 g, 208.00 mol), and the reaction mixture was refluxed for 4 hrs. The reaction mixture was concentrated and the solid was collected by filtration to give 2-cyano-3-(6-methyl-pyridin-3-ylamino)-acrylic acid ethyl ester (21.0 g). The filtrate was concentrated and the residue was then purified by Biotage column, eluting with a gradient of 30-75% AcOEt in nHex to give 2-cyano-3-(6-methyl-pyridin-3-ylamino)-acrylic acid ethyl ester (7.6 g, total yield: 28.6 g, 89.0%) which was used in the next step without further purification.

6-Methyl-4-oxo-1,4-dihydro-[1,5]naphthyridine-3-carbonitrile (4): The suspension of 2-cyano-3-(6-methyl-pyridin-3-ylamino)-acrylic acid ethyl ester (8.8 g, 38.05 mmol) in diphenylether (190 mL) was heated under refluxing for 5 hrs. After cooling to room temperature, the reaction mixture was poured into nHexane (800 mL) and the solid was collected by filtration and washed with cold THF to give 6-methyl-4-oxo-1,4-dihydro-[1,5]naphthyridine-3-carbonitrile (3.86 g, 54.8%). HR-MS-EI (+) m/e calcd for $C_{10}H_7N_3O$ (M+) 185.0589. found 185.0591.

4-Chloro-6-methyl-[1,5]naphthyridine-3-carbonitrile (5): The suspension of 6-methyl-4-oxo-1,4-dihydro-[1,5]naphthyridine-3-carbonitrile (1.47 g, 7.93 mmol) in $POCl_3$ (25 mL) was heated under refluxing for 2 hrs. After cooling to room temperature, the reaction mixture was quenched with ice water and basified with $NH_4OH$ followed by extraction with AcOEt. The organic layer was washed with brine and dried over NaSO4, and concentrated to give 4-chloro-6-methyl-[1,5]naphthyridine-3-carbonitrile as a brown solid (0.92 g, 57.1%). HR-MS-EI (+) m/e calcd for $C_{10}H_6ClN_3$ (M+) 203.0250. found 203.0252.

4-Isopropoxy-6-methyl-[1,5]naphthyridine-3-carbonitrile (6): To a 50 mL flask placed with KH (30%, 685 mg, 6.0 mmol, pre-washed with nHex) was added a solution of anhydrous isopropanol (0.76 mL, 10.0 mmol) in anhydrous THF (5 mL) at room temperature under argon. The reaction mixture was cooled to –20° C. 4-chloro-6-methyl-[1,5]naphthyridine-3-carbonitrile (407.0 mg, 2.0 mmol) in THF (8 mL) was added dropwise and the reaction mixture was stirred at –20° C. to r.t for 30 min. The reaction mixture was quenched with sat.NH4Cl and extracted with AcOEt (100 mL×3). The combined organic layers was dried over Na2SO4 and concentrated to give the crude product which was purified by flash column (AcOEt/Hex=1/3~3/2) to give 4-Isopropoxy-6-methyl-[1,5]naphthyridine-3-carbonitrile as white solid (240.0, 52.8%) which was used in the next step without further purification.

6-Formyl-4-isopropoxyl-[1,5]Naphthyridine-3-carbonitrile (7): To a solution of 4-isopropoxy-6-methyl-[1,5]naphthyridine-3-carbonitrile (260.0 mg, 1.14 mmol) in 1,4-dioxane was added $SeO_2$ (165.0 mg, 1.48 mmol) and the reaction mixture was refluxed for 3.5 hrs, when the TLC showed no starting material left, then cooled to room temperature and filtered through celite. The solid was washed with hot AcOEt and the filtrate was then concentrated to give 6-formyl-4-isopropoxy-[1,5]naphthyridine-3-carbonitrile as a light yellow solid (270.3 mg, 98.3). HR-MS-EI (+) m/e calcd for $C_{13}H_{11}N_3O_2$ (M+) 241.0851. found 241.0854.

Example 2

6-[2-(2-Chloro-benzylamino)-5-oxo-3,5-dihydro-imidazol-4-ylidenemethyl]-4-isopropoxy-[1,5]naphthyridine-3-carbonitrile

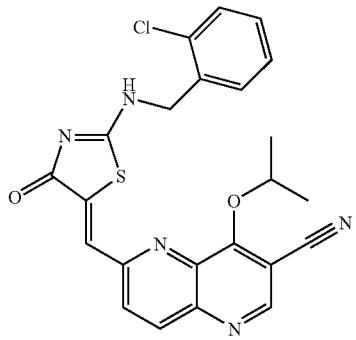

To a mixture of 2-(2-chloro-benzylamino)-thiazol-4-one (48.1 mg, 0.20 mmol) (prepared as described below), AcONa (160 mg, 1.95 mmol), molecular sieves, and 6-formyl-4-isopropoxy-[1,5]naphthyridine-3-carbonitrile (53.1 mg, 0.22 mmol, (see Example 1) in a sealed tube was added AcOH (0.3 mL). The reaction mixture was heated to 85-95° C. (oil bath) for 1.5 h. The reaction mixture was then cooled to r.t. and triturated with water. The solid was collected by filtration and washed with water. The solid was then suspended in hot MeOH (50 mL) and filtered again. The filtrate was concentrated to give a brown solid: 120.3 mg, which was purified by Biotage flash column (1%-6% MeOH in $CH_2Cl_2$) to give 6-[2-(2-chloro-benzylamino)-4-oxo-4H-thiazol-5-ylidenemethyl]-4-isopropoxy-[1,5]naphthyridine-3-carbonitrile as a yellowish solid (32.8 mg, 35.3%). HR-ES (+) m/e calcd for $C_{23}H_{18}ClN_5O_2S$ (M+H)$^+$ 464.0943. found 464.0943.

2-(2-chloro-benzylamino)-thiazol-4-one

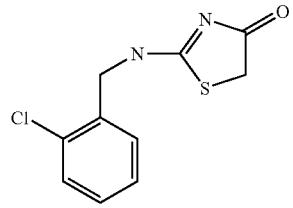

Using a procedure similar to that described in Example 5, 2-(2-benzylamino)-thiazol-4-one was obtained from 2-chloro-benzylamine (Aldrich), rhodanine, mercuric chloride and DIEA LC-MS m/e 241 (MH$^+$).

Example 3

4-Isopropoxy-6-[4-oxo-2-(2-phenyl-cyclopropylamino)-4H-thiazol-5-ylidenemethyl]-[1,5]naphthyridine-3-carbonitrile

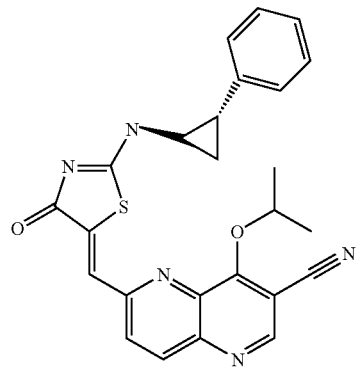

To a mixture of 2-(trans)-phenylcyclopylamino-thiazol-4-one (38.0 mg, 0.16 mmol (prepared as described below), AcONa (160 mg, 1.95 mmol), and 6-formyl-4-isopropoxy-[1,5]naphthyridine-3-carbonitrile (68.2 mg, 0.28 mmol)(see Example 1), in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt (20 mL) and filtered through a glass. The solid was washed with AcOEt and dried to give 4-isopropoxy-6-[4-oxo-2-(2-phenyl-cyclopropylamino)-4H-thiazol-5-ylidenemethyl]-[1,5] naphthyridine-3-carbonitrile as a yellowish solid (34.8 mg, 46.7%). HR-ES (+) m/e calcd for $C_{25}H_{21}N_5O_2S$ (M+H)$^+$ 456.1489. found 456.1488.

2-((1R,2S)-2-phenyl-cyclopropylamino)-thiazol-4-one

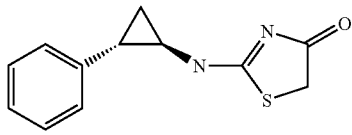

Using a procedure similar to that described in Example 5, 2-((1R,2S)-2-phenyl-cyclopropylamino)-thiazol-4-one was obtained from (1R,2S)-2-phenyl-cyclopropylamine hydrochloride (Aldrich), rhodanine, mercuric chloride and DIEA. LC-MS m/e 232 (MH$^+$).

Example 4

4-Isopropoxy-6-{4-oxo-2-[(thiophen-2-ylmethyl)-amino]-4H-thiazol-5-ylidenemethyl}-[1,5]naphthyridine-3-carbonitrile

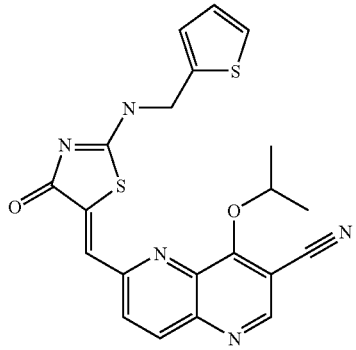

To a mixture of 2-[(thiophen-2-ylmethyl)-amino]-thiazol-4-one (34.0 mg, 0.16 mmol, (prepared as described below), AcONa (160 mg, 1.95 mmol), and 6-formyl-4-isopropoxy-[1,5]naphthyridine-3-carbonitrile (57.9 mg, 0.24 mmol) (see Example 1) in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt (20 mL) and filtered. The solid was washed with AcOEt and dried to give 4-isopropoxy-6-{4-oxo-2-[(thiophen-2-ylmethyl)-amino]-4H-thiazol-5-ylidenemethyl}-[1,5]naphthyridine-3-carbonitrile as a light brown solid (35.4 mg, 50.8%). HR-ES (+) m/e calcd for $C_{21}H_{17}N_5O_2S_2$ (M+H)$^+$ 436.0897. found 436.0895.

2-(thiophen-2-ylmethyl)-amino)-thiazol-4-one

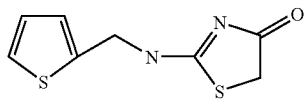

Using a procedure similar to that described in Example 5, 2-(thiophen-2-ylmethyl-amino)-thiazol-4-one was obtained starting with thiophen-2-ylmethyl-amine (Aldrich), rhodanine, mercuric chloride and DIEA. LC-MS m/e 259 (MH$^+$).

Example 5

4-Isopropoxy-6-{2-[(3-methyl-thiophen-2-ylmethyl)-amino]-4-oxo-4H-thiazol-5-ylidenemethyl}-[1,5]naphthyridine-3-carbonitrile

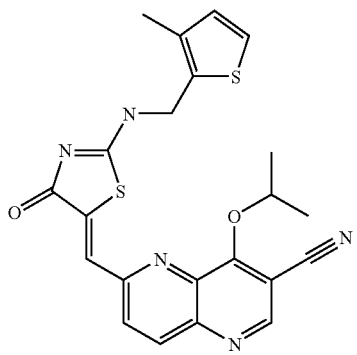

To a mixture of 2-[(3-methyl-thiophen-2-ylmethyl)-amino]-thiazol-4-one (36.2 mg, 0.16 mmol) (prepared as described below), AcONa (160 mg, 1.95 mmol), and 6-formyl-4-isopropoxy-[1,5]naphthyridine-3-carbonitrile (50.2 mg, 0.21 mmol) (see Example 1) in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt (20 mL) and filtered through a glass. The solid was washed with AcOEt and dried to give 4-isopropoxy-6-{2-[(3-methyl-thiophen-2-ylmethyl)-amino]-4-oxo-4H-thiazol-5-ylidenemethyl}-[1,5]naphthyridine-3-carbonitrile as a light brown solid (22.6 mg, 32.4%). HR-ES (+) m/e calcd for $C_{22}H_{19}N_5O_2S_2$ (M+H)$^+$ 450.1053. found 450.1051.

2-[(3-methyl-thiophen-2-ylmethyl)-amino]-thiazol-4-one

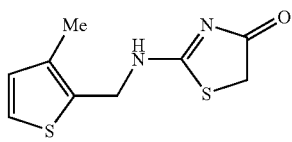

To a solution of 3-methyl-thiophen-2-ylmethylamine (700 mg, 5.5 mmol) (Maybridge) and rhodanine (732 mg, 5.5 mmol) in acetonitrile (30 mL) was added diisopropylethylamine (DIEA) (1.91 mL, 11 mmol) at room temperature. Then, this solution was cooled to 0° C. and mercuric chloride (1.52 g, 5.6 mmol) was added in one portion. After addition, the suspension was allowed to warm to room temperature and stirred for 3 days. The resulting black solids were filtered through a plug of celite and washed with acetonitrile (200 mL) and ethyl acetate (250 mL). The filtrates were removed under the vacuum and the crude residue was dissolved in dichloromethane (150 mL) and washed with water and brine solution. After drying over magnesium sulfate, the filtrate was removed under the vacuum and the residue was dissolved in dichloromethane (10 mL) and diluted with hexanes (10 mL). After overnight storage in the refrigerator, the solids were collected by filtration and washed with dichloromethane. After drying in air, 390 mg (31.5% yield) of 2-[(3-methyl-thiophen-2-ylmethyl)-amino]-thiazol-4-one was isolated as a light yellow amorphous solid: EL-HRMS m/e calcd for $C_9H_{10}N_2OS_2$ (M+) 226.0235. found 226.0232.

Example 6

6-[2-(2-Chloro-6-methyl-benzylamino)-4-oxo-4H-thiazol-5-ylidenemethyl]-4-isopropoxy-[1,5]naphthyridine-3-carbonitrile

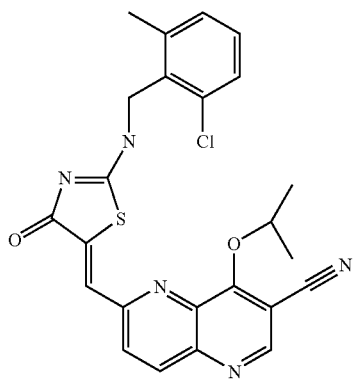

To a mixture of 2-(2-chloro-6-methyl-benzylamino)-thiazol-4-one (40.81 mg, 0.16 mmol) (prepared as described below), AcONa (160 mg, 1.95 mmol), and 6-formyl-4-isopropoxy-[1,5]naphthyridine-3-carbonitrile (50.2 mg, 0.21 mmol) (see Example 1) in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt (20 mL) and filtered. The filtrate was then concentrated to give a brown solid (45.7 mg), which was re-crystallized from AcOEt-MeOH to give 6-[2-(2-chloro-6-methyl-benzylamino)-4-oxo-4H-thiazol-5-ylidenemethyl]-4-isopropoxy [1,5]naphthyridine-3-carbonitrile as a light brown solid (12.8 mg, 16.7%). HR-ES (+) m/e calcd for $C_{24}H_{20}ClN_5O_2S$ (M+H)+ 478.1099. found 478.1097.

2-(2-chloro-6-methyl-benzylamino)-thiazol-4-one

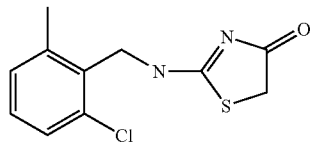

Using a procedure similar to that described in Example 5, 2-(2-chloro-6-methyl-benzylamino)-thiazol-4-one was prepared from 2-chloro-6-methyl-benzylamine (Lancaster), rhodanine, mercuric chloride and DIEA. LC-MS m/e 259 (MH+).

Example 7

6-{2-[2-(3-Fluoro-phenyl)-ethylamino]-4-oxo-4H-thiazol-5-ylidenemethyl}-4-isopropoxy-[1,5]naphthyridine-3-carbonitrile

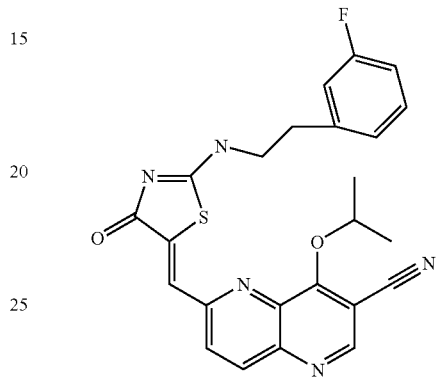

To a mixture of 2-[2-(3-fluoro-phenyl)-ethylamino]-thiazol-4-one (38.1 mg, 0.16 mmol) (prepared as described below), AcONa (160 mg, 1.95 mmol), and 6-formyl-4-isopropoxy-[1,5]naphthyridine-3-carbonitrile (50.2 mg, 0.21 mmol) (see Example 1) in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt (20 mL) and filtered through a glass filter. The solid was washed with AcOEt and dried to give 6-{2-[2-(3-fluoro-phenyl)-ethylamino]-4-oxo-4H-thiazol-5-ylidenemethyl}-4-isopropoxy-[1,5]naphthyridine-3-carbonitrile as a light green solid (30.7 mg, 41.6%). HR-ES (+) m/e calcd for $C_{24}H_{20}FN_5O_2S$ (M+H)+ 462.1395. found 462.1395.

2-[2-(3-fluoro-phenyl)-ethylamino]-thiazol-4-one

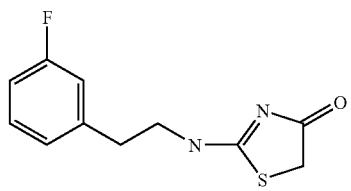

Using a procedure similar to that described in Example 5, 2-[2-(3-fluoro-phenyl)-ethylamino]-thiazol-4-one was obtained from (3-flurophenyl)-ethylamine (Aldrich), rhodanine, mercuric chloride and DIEA. HR-ES (+) m/e calcd for $C_{11}H_{11}FN_2OS$ (M+H)+ 239.0649. found 239.0647.

Example 8

6-[2-(2-Chloro-4-fluoro-benzylamino)-4-oxo-4H-thiazol-5-ylidenemethyl]-4-isopropoxy-[1,5]naphthyridine-3-carbonitrile

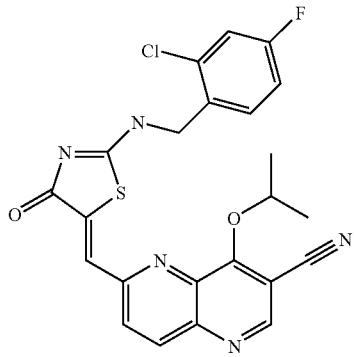

To a mixture of 2-(2-chloro-4-fluoro-benzylamino)-thiazol-4-one (41.4 mg, 0.16 mmol) (prepared as described below), AcONa (160 mg, 1.95 mmol), and 6-formyl-4-isopropoxy-[1,5]naphthyridine-3-carbonitrile (50.2 mg, 0.21 mmol) (see Example 1) in a sealed tube was added AcOH (0.3 mL). The reaction mixture was heated to 80° C. (oil bath) for 5 hrs. The reaction mixture was then cooled to r.t. and triturated with water. The solid was collected by filtration and washed with water. The solid was then suspended in AcOEt, re-filtered through a paper filter to give 6-[2-(2-chloro-4-fluoro-benzylamino)-4-oxo-4H-thiazol-5-ylidenemethyl]-4-isopropoxy-[1,5]naphthyridine-3-carbonitrile as a light brown solid (19.2 mg, 24.9%). HR-ES (+) m/e calcd for $C_{23}H_{17}FClN_5O_2S$ (M+H)$^+$ 482.0849. found 482.0848.

2-(2-chloro-4-fluoro-benzylamino)-thiazol-4-one

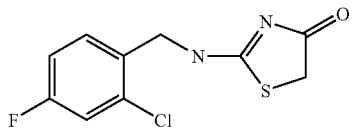

Using a procedure similar to that described in Example 5, 2-(2-chloro-4-fluoro-benzylamino)-thiazol-4-one was obtained from 2-chloro-4-fluoro-benzylamine (Lancaster), rhodanine, mercuric chloride and DIEA. LC-MS m/e 259 (MH$^+$).

Example 9

6-[2-(2,4-Bis-trifluoromethyl-benzylamino)-5-oxo-3,5-dihydro-imidazol-4-ylidenemethyl]-4-isopropoxy-[1,5]naphthyridine-3-carbonitrile

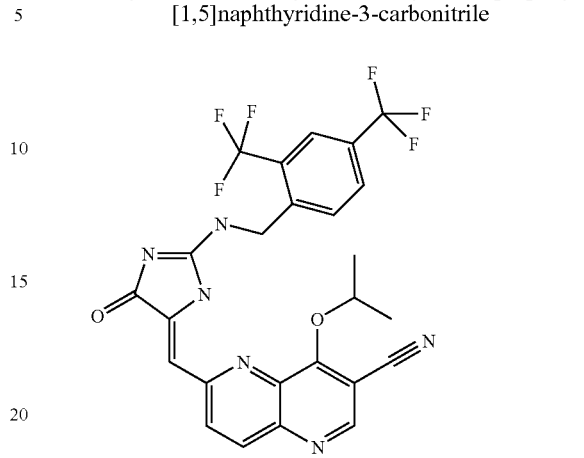

To a mixture of 2-(2,4-bis-trifluoromethyl-benzylamino)-4-oxo-4,5-dihydro-imidazole-1-carboxylic acid benzyl ester (82.7 mg, 0.18 mmol) (prepared as described in C-H Kwon et al. *J. Med. Chem.* 1991, 34, 1845-1849), 6-formyl-4-isopropoxy-[1,5]naphthyridine-3-carbonitrile (45.6 mg, 0.19 mmol) (see Example 1) and iPrOH (5 mL) in a 25-mL round bottom flask was added piperidine (0.05 mL) and the suspension was then heated under refluxing for 5 h to give a brown solution. The reaction mixture was cooled to r.t. and concentrated to give a light yellow solid, 66.3 mg, which was purified by flash column purification to give 6-[2-(2,4-bis-trifluoromethyl-benzylamino)-5-oxo-3,5-dihydro-imidazol-4-ylidenemethyl]-4-isopropoxy-[1,5]naphthyridine-3-carbonitrile, as a light yellow solid, 20.6 mg (20.9%). HR-ES (+) m/e calcd for $C_{25}H_{18}F_6N_6O_2$ (M+H)$^+$ 549.1468. found 549.1472.

Example 10

4-Isopropoxy-6-[5-oxo-2-(2-trifluoromethyl-benzylamino)-3,5-dihydro-imidazol-4-ylidenemethyl]-[1,5]naphthyridine-3-carbonitrile

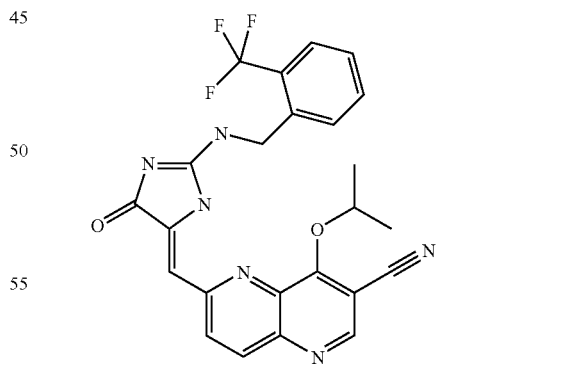

To a mixture of 4-oxo-2-(2-trifluoromethyl-benzylamino)-4,5-dihydro-imidazole-1-carboxylic acid benzyl ester (70.4 mg, 0.18 mmol) (prepared as described in C-H Kwon et al. *J. Med. Chem.* 1991, 34, 1845-1849), 6-formyl-4-isopropoxy-[1,5]naphthyridine-3-carbonitrile (56.5 mg, 0.23 mmol) (see Example 1) and iPrOH (5 mL) in a 25-mL round bottom flask was added piperidine (0.05 mL) and the suspension was then heated under refluxing for 5 h to give a brown solution. The reaction mixture was cooled to r.t. and concentrated to give a light yellow solid, 66.3 mg, which was purified by flash column purification to give 4-isopropoxy-6-[5-oxo-2-(2-trifluoromethyl-benzylamino)-3,5-dihydro-imidazol-4-ylidenemethyl]-[1,5]naphthyridine-3-carbonitrile, as a light yellow solid, 18.6 mg (21.5%). HR-ES (+) m/e calcd for $C_{24}H_{19}F_3N_6O_2$ (M+H)$^+$ 481.1595. found 481.1595.

Example 11

6-{4-Oxo-2-[(thiophen-2-ylmethyl)-amino]-4H-thiazol-5-ylidenemethyl}-[1,5]naphthyridine-3-carbonitrile

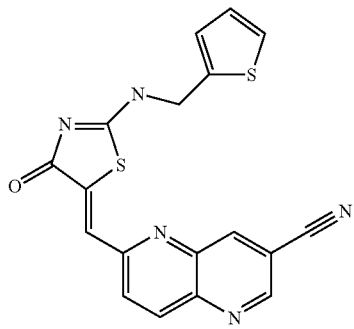

To a mixture of 2-[(thiophen-2-ylmethyl)-amino]-thiazol-4-one one (34.0 mg, 0.16 mmol) (see Example 4), AcONa (160 mg, 1.95 mmol), and 6-formyl-[1,5]naphthyridine-3-carbonitrile (38.5 mg, 0.21 mmol) (prepared as described below) in a sealed tube was added AcOH (0.3 mL). The reaction mixture was heated to 100° C. (oil bath) for 4.5 hrs. The reaction mixture was then cooled to r.t. and triturated with water. The solid was collected by filtration and washed with water. The solid was then dissolved in DMF (1 mL) with heating and then poured into ice water, and filtered. The solid was washed with AcOEt and dried to give 6-{4-oxo-2-[(thiophen-2-ylmethyl)-amino]-4H-thiazol-5-ylidenemethyl}-[1,5]naphthyridine-3-carbonitrile as a dark brown solid (12.8 mg, 21.2%). HR-ES (+) m/e calcd for $C_{18}H_{11}N_5OS_2$ (M+H)$^+$ 400.0297. found 400.0298.

6-Formyl-[1,5]naphthyridine-3-carbonitrile(14)

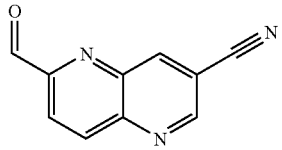

6-Methyl-[1,5]naphthyridine-3-carbonitrile (13): To a solution of 4-chloro-6-methyl-[1,5]naphthyridine-3-carbonitrile (200.0 mg, 0.98 mmol) (compound 5, see Example 1)in AcOH (20 mL) was added Zinc dust (156.1 mg, 2.40 mmol) and the reaction mixture was stirred at r.t. for 2 hrs. The reaction mixture was filtered through celite and the filtrate was then concentrated. The residue was dissolved in AcOEt and washed with water, Sat. Na2CO3, brine and dried to yield 6-methyl-[1,5]naphthyridine-3-carbonitrile as a light brown solid (120.0 mg, 71.3%). HR-MS-EI (+) m/e calcd for $C_{10}H_7N_3$(M+) 169.0640. found 169.0639.

6-Formyl-[1,5]naphthyridine-3-carbonitrile (14): To a solution of 6-methyl-[1,5]naphthyridine-3-carbonitrile (220.0 mg, 1.30 mmol) in 1,4-dioxane was added $SeO_2$ (187.6 mg, 1.70 mmol) and the reaction mixture was refluxed for 2 hrs, when the TLC showed no starting material left, then cooled to room temperature and filtered through celite. The solid was washed with hot AcOEt and the filtrate was then concentrated to give 6-formyl-[1,5]naphthyridine-3-carbonitrile as a light yellow solid (238.1 mg, 100.0%). HR-MS-EI (+) m/e calcd for $C_{10}H_5N_3O$ (M+) 183.0433. found 183.0433

Example 12

6-[4-oxo-2-(2-phenyl-cyclopropylamino)-4H-thiazol-5-ylidenemethyl]-[1,5]naphthyridine-3-carbonitrile

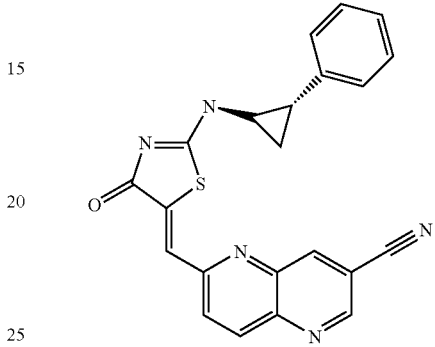

To a mixture of 2-(trans)-phenylcyclopylamino-thiazol-4-one (38.0 mg, 0.16 mmol) (see Example 3), AcONa (160 mg, 1.95 mmol), and 6-formyl-[1,5]naphthyridine-3-carbonitrile (38.5 mg, 0.21 mmol) (see Example 11), in a sealed tube was added AcOH (0.3 mL). The reaction mixture was heated to 100° C. (oil bath) for 5 hrs. The reaction mixture was then cooled to r.t. and triturated with water. The solid was collected by filtration and washed with water acetone and ether to give 6-[4-oxo-2-(2-phenyl-cyclopropylamino)-4H-thiazol-5-ylidenemethyl]-[1,5]naphthyridine-3-carbonitrile as a yellowish solid (13.7 mg, 18.3%). HR-ES (+) m/e calcd for $C_{22}H_{15}N_5OS$ (M+H)$^+$ 398.1070. found 398.1071.

Example 13

6-{(2-[(3-Methyl-thiophen-2-ylmethyl)-amino]-4-oxo-4H-thiazol-5-ylidenemethyl}-[1,5]naphthyridine-3-carbonitrile

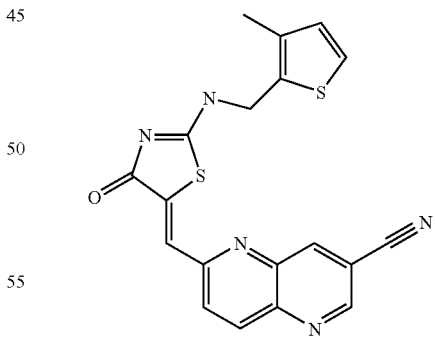

To a mixture of 2-[(3-methyl-thiophen-2-ylmethyl)-amino]-thiazol-4-one (21.7 mg, 0.10 mmol), AcONa (160 mg, 1.95 mmol) (see Example 5), and 6-formyl-[1,5]naphthyridine-3-carbonitrile (22.0 mg, 0.12 mmol) (see Example 11) in a sealed tube was added AcOH (0.3 mL). The reaction mixture was heated to 100° C. (oil bath) for 1.5 hrs. The reaction mixture was then cooled to r.t. and triturated with water. The solid was collected by filtration and washed with water, AcOEt and ether to give 6-{2-[(3-methyl-thiophen-2-ylmethyl)-amino]-4-oxo-4H-thiazol-5-ylidenemethyl}-[1, 5]naphthyridine-3-carbonitrile as a light brown solid (14.0 mg, 35.8%). HR-ES (+) m/e calcd for $C_{19}H_{13}N_5OS_2$ (M+H)$^+$ 414.0454. found 414.0452.

Example 14

6-(2-Amino-4-oxo-4H-thiazol-5-ylidenemethyl)-[1,5]naphthyridine-3-carbonitrile

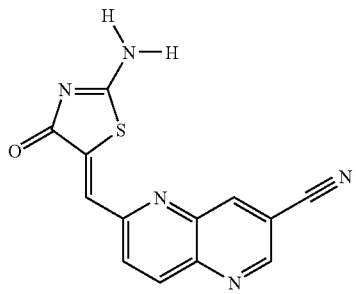

To a mixture of pseudothiohydantoin (Aldrich, 97%, 23.2 mg, 0.20 mmol), AcONa (160 mg, 1.95 mmol), molecular sieves, and 6-formyl-[1,5]naphthyridine-3-carbonitrile (38.5 mg, 0.21 mmol) (see Example 11) in a sealed tube was added AcOH (0.3 mL). The reaction mixture was heated to 120° C. for 3.5 hrs. The reaction mixture was then cooled to r.t. and triturated with water. The solid was collected by filtration and washed with water, AcOEt and ether to give 6-(2-amino-4-oxo-4H-thiazol-5-ylidenemethyl)-[1,5]naphthyridine-3-carbonitrile as a yellowish solid (30.3 mg, 44.6%). LR-ES (+) m/e 282 (M+H).

Example 15

6-{2-[2-(3-fluoro-phenyl)-ethylamino]-4-oxo-4H-thiazol-5-ylidenemethyl}-[1,5]naphthyridine-3-carbonitrile

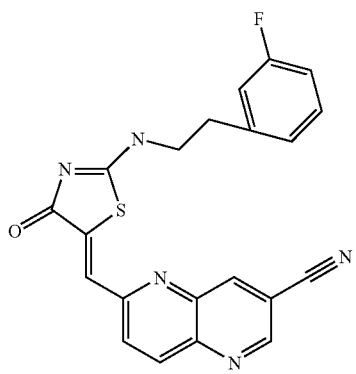

To a mixture of 2-[2-(3-fluoro-phenyl)-ethylamino]-thiazol-4-one (40.9 mg, 0.17 mmol) (see Example 7) AcONa (160 mg, 1.95 mmol), and 6-formyl-[1,5]naphthyridine-3-carbonitrile (33.6 mg, 0.18 mmol) (see Example 11) in a sealed tube was added AcOH (0.3 mL). The reaction mixture was heated to 120° C. (oil bath) for 2 hrs. The reaction mixture was then cooled to r.t. and triturated with water. The solid was collected by filtration and washed with water, AcOEt and ether to give 6-{2-[2-(3-fluoro-phenyl)-ethylamino]-4-oxo-4H-thiazol-5-ylidenemethyl}-[1,5]naphthyridine-3-carbonitrile as a dark brown solid (20.8 mg, 30.1%). HR-ES (+) m/e calcd for $C_{21}H_{14}FN_5OS$ (M+H)$^+$ 404.0976. found 404.0977.

Example 16

6-[2-(2-Chloro-benzylamino)-5-oxo-3,5-dihydro-imidazol-4-ylidenemethyl]-[1,5]naphthyridine-3-carbonitrile

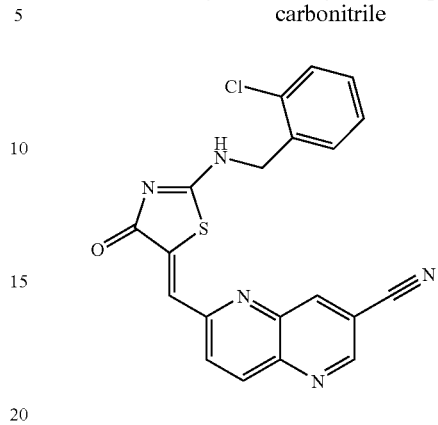

To a mixture of 2-(2-chloro-benzylamino)-thiazol-4-one (40.9 mg, 0.17 mmol) (see Example 2), AcONa (160 mg, 1.95 mmol), and 6-formyl-4-isopropoxy-[1,5]naphthyridine-3-carbonitrile (53.1 mg, 0.22 mmol) (see Example 11) in a sealed tube was added AcOH (0.3 mL). The reaction mixture was heated to 120° C. (oil bath) for 2 hrs. The reaction mixture was then cooled to r.t. and triturated with water. The solid was collected by filtration and washed with water acetone and ether to give 6-[2-(2-chloro-benzylamino)-4-oxo-4H-thiazol-5-ylidenemethyl]-[1,5]naphthyridine-3-carbonitrile as a dark brown solid (20.8 mg, 30.1%). HR-ES (+) m/e calcd for $C_{20}H_{12}ClN_5OS$ (M+H)$^+$ 406.0524. found 406.0525.

Example 17

6-[2-(2-Chloro-6-methyl-benzylamino)-4-oxo-4H-thiazol-5-ylidenemethyl]-[1,5]naphthyridine-3-carbonitrile

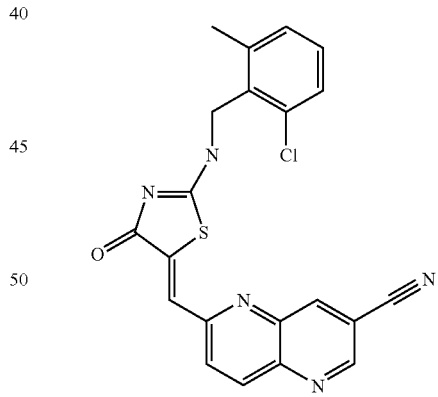

To a mixture of 2-(2-chloro-6-methyl-benzylamino)-thiazol-4-one (40.81 mg, 0.16 mmol) (see Example 6), AcONa (160 mg, 1.95 mmol), and 6-formyl-[1,5]naphthyridine-3-carbonitrile (33.6 mg, 0.18 mmol) (see Example 11) in a sealed tube was added AcOEt (0.3 mL). The reaction mixture was heated to 110° C. (oil bath) for 1 hr. The reaction mixture was then cooled to r.t. and triturated with water. The solid was collected by filtration and washed with water, AcOEt and ether to give a brown solid (45.7 mg), which was re-crystallized from AcOEt-MeOH to give 6-[2-(2-chloro-6-methyl-benzylamino)-4-oxo-4H-thiazol-5-ylidenemethyl]-[1,5]naphthyridine-3-carbonitrile as a brown solid (39.5 mg, 51.6%). HR-ES (+) m/e calcd for $C_{21}H_{14}ClN_5OS$ (M+H)+ 420.0681. found 420.0680.

Example 18

6-[2-(2-Chloro-4-fluoro-benzylamino)-4-oxo-4H-thiazol-5-ylidenemethyl]-[1,5]naphthyridine-3-carbonitrile

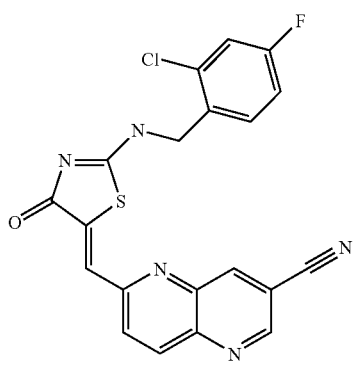

To a mixture of 2-(2-chloro-4-fluoro-benzylamino)-thiazol-4-one (41.4 mg, 0.16 mmol) (see Example 8), AcONa (160 mg, 1.95 mmol), and 6-formyl-[1,5]naphthyridine-3-carbonitrile (33.6 mg, 0.18 mmol) (see Example 11) in a sealed tube was added AcOH (0.3 mL). The reaction mixture was heated to 120° C. (oil bath) for 2 hrs. The reaction mixture was then cooled to r.t. and triturated with water. The solid was collected by filtration and washed with water, AcOEt and ether to give 6-[2-(2-chloro-4-fluoro-benzylamino)-4-oxo-4H-thiazol-5-ylidenemethyl]-[1,5]naphthyridine-3-carbonitrile as a light brown solid (22.6 mg, 33.3%). HR-ES (+) m/e calcd for $C_{20}H_{11}FClN_5OS$ (M+Na)+ 446.0249. found 446.0251.

Example 19

6-[2-(3-Chloro-4-fluoro-benzylamino)-4-oxo-4H-thiazol-5-ylidenemethyl]-[1,5]naphthyridine-3-carbonitrile

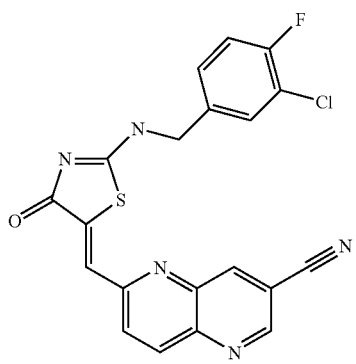

To a mixture of 2-(3-chloro-4-fluoro-benzylamino)-thiazol-4-one (41.4 mg, 0.16 mmol) (prepared as described below) AcONa (160 mg, 1.95 mmol), and 6-formyl-[1,5] naphthyridine-3-carbonitrile (33.6 mg, 0.18 mmol) (see Example 11) in a sealed tube was added AcOH (0.3 mL). The reaction mixture was heated to 120° C. (oil bath) for 3 hrs. The reaction mixture was then cooled to r.t. and triturated with water. The solid was collected by filtration and washed with water, AcOEt and ether to give 6-[2-(3-chloro-4-fluoro-benzylamino)-4-oxo-4H-thiazol-5-ylidenemethyl]-[1,5]naphthyridine-3-carbonitrile as a light brown solid (30.6 mg, 45.1%). HR-ES (+) m/e calcd for $C_{20}H_{11}FClN_5OS$ (M+H)+ 424.0430. found 424.0431.

2-(3-chloro-4-fluoro-benzylamino)-thiazol-4-one

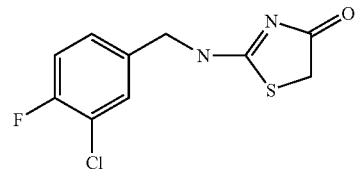

Using a procedure similar to that described in Example 5, 2-(3-chloro-4-fluoro-benzylamino)-thiazol-4-one was prepared from 3-chloro-4-fluoro-benzylamine (Lancaster), rhodanine, mercuric chloride and DIEA. LC-MS m/e 259 (MH+).

Example 20

5-(8-Isopropoxy-[1,5]naphthyridin-2-ylmethylene)-2-(2-phenyl-cyclopropylamino)-thiazol-4-one

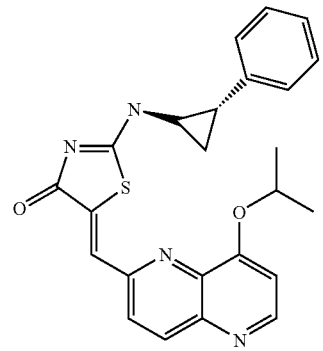

To a mixture of 2-(trans)-phenylcyclopylamino-thiazol-4-one (76.0 mg, 0.32 mmol) (see Example 3) AcONa (160 mg, 1.95 mmol), and 8-isopropoxy-[1,5]naphthyridine-2-carbaldehyde (77.8 mg, 0.36 mmol) (prepared as described below) in a sealed tube was added AcOH (0.4 mL). The reaction mixture was heated to 100° C. (oil bath) for 4 hrs. The reaction mixture was then cooled to r.t. and triturated with water. The solid was collected by filtration and washed with water, acetone and ether to give 5-(8-isopropoxy-[1,5] naphthyridin-2-ylmethylene)-2-(2-phenyl-cyclopropylamino)-thiazol-4-one as a yellowish solid (101.5 mg, 73.7%). HR-ES (+) m/e calcd for $C_{24}H_{22}N_4O_2S$ (M+H)+ 431.1536. found 431.1537.

8-isopropoxy-[1,5]naphthyridine-2-carbaldehyde (Scheme 5)

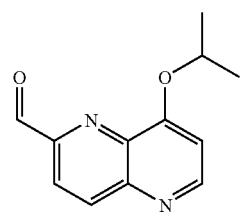

2-[(6-Methyl-pyridin-3-ylamino)-methylene]-malonic acid diethyl ester: To a solution of 5-amino-2-picoline (ChemPacific, 10.80 g, 99.87 mmol) (in toluene (125 mL) was added diethylthoxymethylenemalonate (Fluka, 26.69 g, 119.80 mol), and the reaction mixture was refluxed for 5 hrs. The reaction mixture was concentrated and the solid was collected by filtration to give 2-[(6-methyl-pyridin-3-ylamino)-methylene]-malonic acid diethyl ester (24.0 g). The filtrate was concentrated and the residue was then purified by Biotage column, eluting with a gradient of 30-75% AcOEt in nHex to give 2-[(6-methyl-pyridin-3-ylamino)-methylene]-malonic acid diethyl ester (2.9 g). Total yield: 26.9 g, 97%. HR-ES (+) m/e calcd for $C_{14}H_{18}N_2O_4$ (M+H)$^+$ 279.1340. found 279.1339.

4-Hydroxy-6-methyl-[1,5]naphthyridine-3-carboxylic acid ethyl ester: The suspension of 2-[(6-methyl-pyridin-3-ylamino)-methylene]-malonic acid diethyl ester (24.0 g, 86.23 mmol) in diphenylether (300 mL) was heated under refluxing for 3 hrs. After cooling to room temperature, the reaction mixture was poured into nHexane (1000 mL) and the solid was collected by filtration to give 4-hydroxy-6-methyl-[1,5]naphthyridine-3-carboxylic acid ethyl ester (8.3 g, 42%). HR-MS-EI (+) m/e calcd for $C_{12}H_{12}N_2O_3$ (M+) 232.0848. found 232.0846.

4-Hydroxy-6-methyl-[1,5]naphthyridine-3-carboxylic acid: The suspension of 4-hydroxy-6-methyl-[1,5]naphthyridine-3-carboxylic acid ethyl ester (4.15 g, 17.87 mmol) in 10% KOH (40 mL) was stirred at room temperature for 3.5 hrs. 3 N HCl was added to adjust the pH to 7. The solid was collected by filtration to give 4-hydroxy-6-methyl-[1,5]naphthyridine-3-carboxylic acid (2.58 g, 72%). HR-ES (+) m/e calcd for $C_{10}H_8N_2O_3$ (M+H) 205.0608. found 205.0608.

6-Methyl-[1,5]naphthyridin-4-ol: The suspension of 4-hydroxy-6-methyl-[1,5]naphthyridine-3-carboxylic acid (2.58 g, 12.64 mmol) in diphenylether (100 mL) was heated under refluxing for 4 hrs. After cooling to room temperature, the reaction mixture was poured into a mixture of nHexane (400 mL) and petroleum ether (200 mL). The brown solid was collected by filtration to give 6-methyl-[1,5]naphthyridin-4-ol (1.71 g, 86%). HR-MS-EI (+) m/e calcd for $C_9H_8N_2O$ (M+) 160.0637. found 160.0638

8-Chloro-2-methyl-[1,5]naphthyridine: The suspension of 6-methyl-[1,5]naphthyridin-4-ol (1.60 g, 9.99 mmol) in POCl$_3$ (25 mL) was heated under refluxing for 2 hrs. After cooling to room temperature, the reaction mixture was quenched with ice water and basified with NH$_4$OH followed by extraction with AcOEt. The organic layer was washed with brine and dried over NaSO4, and concentrated to give 8-chloro-2-methyl-[1,5]naphthyridine as a brown solid (1.2 g, 67%). HR-MS-EI (+) m/e calcd for $C_9H_7N_2Cl$ (M+) 178.0298. found 178.0297.

8-Isopropoxy-2-methyl-[1,5]naphthyridine: To a 100 mL flask placed with KH (30%, 2.7 g, 20.15 mmol, pre-washed with nHex) was added a solution of anhydrous isopropanol (2.04 g, 33.59 mmol) in anhydrous THF (15 mL) at room temperature under argon. The reaction mixture was cooled to −20° C. 8-chloro-2-methyl-[1,5]naphthyridine (1.20 g, 6.72 mmol) in THF (20 mL) was added dropwise and the reaction mixture was stirred at −20° C. to r.t for 2 hrs. The reaction mixture was poured into 20 mL ice-water and extracted with AcOEt (100 mL×3). The combined organic layers was dried over Na2SO4 and concentrated to give the crude product which was purified by flash column (AcOEt/Hex=1/3~3/2) to give 8-isopropoxy-2-methyl-[1,5]naphthyridine as white solid (0.34 g, 25%). HR-MS-EI (+) m/e calcd for $C_{12}H_{14}N_2O$ (M+) 202.1106. found 202.1107.

8-Isopropoxy-[1,5]naphthyridine-2-carbaldehyde: To a solution of 8-isopropoxy-2-methyl-[1,5]naphthyridine (1.13 g, 5.60 mmol) in 1,4-dioxane (40 mL) was added SeO$_2$ (0.80 g, 7.20 mmol) and the reaction mixture was refluxed for 2 hrs, when the TLC showed no starting material left, then cooled to room temperature and filtered through celite. The solid was washed with hot AcOEt and the filtrate was then concentrated to give 8-isopropoxy-[1,5]naphthyridine-2-carbaldehyde as a light yellow solid (1.20 g, 100%). HR-MS-EI (+) m/e calcd for $C_{12}H_{12}N_2O_2$ (M+) 216.0899. found 216.0900

Example 21

2-[2-(3-Fluoro-phenyl)-ethylamino]-5-(8-isopropoxy-[1,5]naphthyridin-2-ylmethylene)-thiazol-4-one

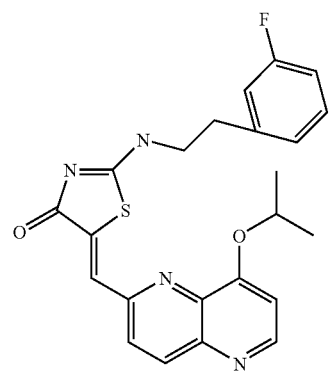

To a mixture of 2-[2-(3-fluoro-phenyl)-ethylamino]-thiazol-4-one (38.1 mg, 0.16 mmol) (see Example 7), AcONa (160 mg, 1.95 mmol), and 8-isopropoxy-[1,5]naphthyridine-2-carbaldehyde (38.9 mg, 0.18 mmol) (see Example 20) in a sealed tube was added AcOH (0.3 mL). The reaction mixture was heated to 100° C. (oil bath) for 4 hrs. The reaction mixture was then cooled to r.t. and triturated with water. The solid was collected by filtration and washed with water, acetone and ether to give 2-[2-(3-fluoro-phenyl)-ethylamino]-5-(8-isopropoxy-[1,5]naphthyridin-2-ylmethylene)-thiazol-4-one as a light green solid (45.9 mg, 65.8%). HR-ES (+) m/e calcd for $C_{23}H_{21}FN_4O_2S$ (M+H)$^+$ 437.1442. found 437.1443.

Example 22

5-(8-Isopropoxy-[1,5]naphthyridin-2-ylmethylene)-2-[(thiophen-2-ylmethyl)-amino]-thiazol-4-one

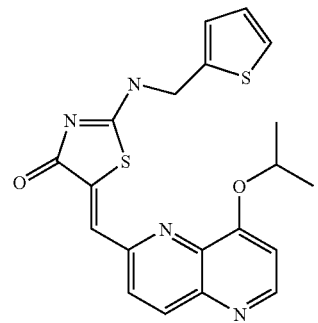

To a mixture of 2-[(thiophen-2-ylmethyl)-amino]-thiazol-4-one one (34.0 mg, 0.16 mmol) (see Example 4), AcONa (160 mg, 1.95 mmol), and 8-isopropoxy-[1,5]naphthyridine-2-carbaldehyde (38.9 mg, 0.18 mmol) (see Example 20) in a sealed tube was added AcOH (0.3 mL). The reaction mixture was heated to 100° C. (oil bath) for 4.5 hrs. The reaction mixture was then cooled to r.t. and triturated with water. The solid was collected by filtration and washed with water, acetone and ether to give 5-(8-isopropoxy-[1,5]naphthyridin-2-ylmethylene)-2-[(thiophen-2-ylmethyl)-amino]-thiazol-4-one as a light brown solid (29.8 mg, 45.4%). HR-ES (+) m/e calcd for $C_{20}H_{18}N_4O_2S_2$ (M+H)$^+$ 411.0944. found 411.0945.

Example 23

2-(2-Chloro-benzylamino)-5-(8-isopropoxy-[1,5]naphthyridin-2-ylmethylene)-thiazol-4-one

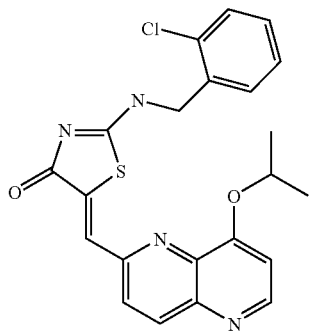

To a mixture of 2-(2-chloro-benzylamino)-thiazol-4-one (38.5 mg, 0.16 mmol) (see Example 2), AcONa (160 mg, 1.95 mmol), molecular sieves, and 8-isopropoxy-[1,5]naphthyridine-2-carbaldehyde (38.9 mg, 0.18 mmol) (see Example 20) in a sealed tube was added AcOH (0.3 mL). The reaction mixture was heated to 100° C. (oil bath) for 5 hrs. The reaction mixture was then cooled to r.t. and triturated with water. The solid was collected by filtration and washed with water. The solid was collected by filtration and washed with water, acetone and ether to give 2-(2-chloro-benzylamino)-5-(8-isopropoxy-[1,5]naphthyridin-2-ylmethylene)-thiazol-4-one as a brown solid (31.4 mg, 44.7%). HR-ES (+) m/e calcd for $C_{22}H_{19}ClN_4O_2S$ (M+H)$^+$ 439.0990. found 439.0987.

Example 24

2-(3-Chloro-4-fluoro-benzylamino)-5-(8-isopropoxy-[1,5]naphthyridin-2-ylmethylene)-thiazol-4-one

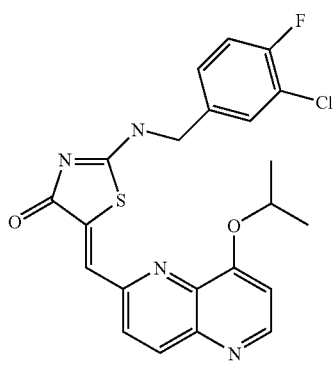

To a mixture of 2-(3-chloro-4-fluoro-benzylamino)-thiazol-4-one (41.4 mg, 0.16 mmol) (see Example 19), AcONa (160 mg, 1.95 mmol), and 8-isopropoxy-[1,5]naphthyridine-2-carbaldehyde (38.9 mg, 0.18 mmol) (see Example 20) in a sealed tube was added AcOH(0.3 mL). The reaction mixture was heated to 100° C. (oil bath) for 2 hrs. The reaction mixture was then cooled to r.t. and triturated with water. The solid was collected by filtration and washed with water, acetone and ether to give 2-(3-chloro-4-fluoro-benzylamino)-5-(8-isopropoxy-[1,5]naphthyridin-2-ylmethylene)-thiazol-4-one as a light brown solid (63.5 mg, 86.9%). HR-ES (+) m/e calcd for $C_{22}H_{18}FClN_4O_2S$ (M+H)$^+$ 457.0896. found 457.0897.

Example 25

2-(2-Chloro-4-fluoro-benzylamino)-5-(8-isopropoxy-[1,5]naphthyridin-2-ylmethylene)-thiazol-4-one

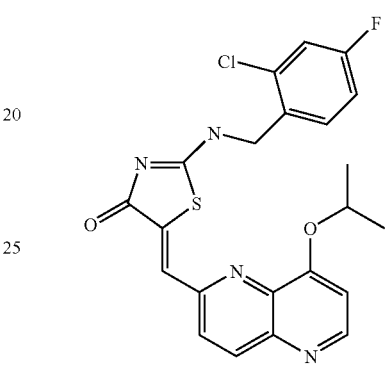

To a mixture of 2-(2-chloro-4-fluoro-benzylamino)-thiazol-4-one (41.4 mg, 0.16 mmol) (see Example 18), AcONa (160 mg, 1.95 mmol), and 8-isopropoxy-[1,5]naphthyridine-2-carbaldehyde (38.9 mg, 0.18 mmol) (see Example 20) in a sealed tube was added AcOH(0.3 mL). The reaction mixture was heated to 100° C. (oil bath) for 3 hrs. The reaction mixture was then cooled to r.t. and triturated with water. The solid was collected by filtration and washed with water, acetone and ether to give 2-(2-chloro-4-fluoro-benzylamino)-5-(8-isopropoxy-[1,5]naphthyridin-2-ylmethylene)-thiazol-4-one as a light brown solid (43.5 mg, 59.5%). HR-ES (+) m/e calcd for $C_{22}H_{18}FClN_4O_2S$ (M+H)$^+$ 457.0896. found 457.0897.

Example 26

[5-(8-Isopropoxy-[1,5]naphthyridin-2-ylmethylene)-4-oxo-4,5-dihydro-thiazol-2-yl]-carbamic acid tert-butyl ester

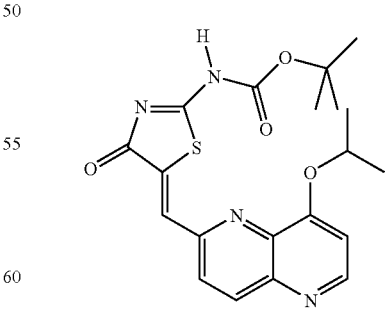

To a suspension of N-Boc-pseudothiohydantoin(138.4 mg, 0.64 mmol (prepared as described below), and 8-isopropoxy-[1,5]naphthyridine-2-carbaldehyde (155.6 mg, 0.72 mmol) (see Example 20) in toluene in a microwave tube was added benzoic acid and piperidine. The reaction mixture was heated to give a light yellow solution and then heated to 140° C. with microwave for 15 min. The reaction mixture was then cooled to r.t. and diluted with toluene. The solid was collected by filtration and washed with toluene, acetone and ether to give [5-(8-isopropoxy-[1,5]naphthyridin-2-ylmethylene)-4-oxo-4,5-dihydro-thiazol-2-yl]-carbamic acid tert-butyl ester as a light brown solid: 125.3 mg (47.2%). HR-ES (+) m/e calcd for $C_{20}H_{22}N_4O_4S$ (M+H)$^+$ 415.1435. found 415.1436.

(4-oxo-4,5-dihydro-thiazol-2-yl)-carbamic acid tert-butyl ester

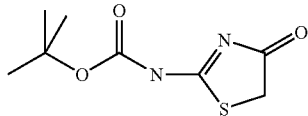

To a suspension of pseudothiohydantoin (Aldrich, 97%, 10.13 g, 84.61 mmol) in acetonitrile (159 mL) were added Di-tert-butyldicarbonate (20.32 g, 93.07 mmol) and DMAP (11.37 g, 93.07 mmol) at room temperature. The resulting mixture was stirred for 15 hrs at room temperature. The precipitated solid was collected by filtration and washed with $CH_2Cl_2$. The filtrate was concentrated and the residue was then purified by Biotage silica gel column to give (4-oxo-4,5-dihydro-thiazol-2-yl)-carbamic acid tert-butyl ester as a white solid (2.75 g, 15.0%). EI-LRMS m/e calcd for $C_8H_{12}N_2O_3S$ (M+) 215.1. found 215.1.

Example 27

2-Amino-5-(8-isopropoxy-[1,5]naphthyridin-2-ylmethylene)-thiazol-4-one

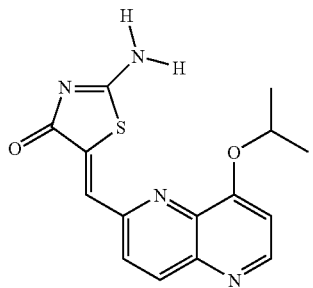

A mixture of [5-(8-isopropoxy-[1,5]naphthyridin-2-ylmethylene)-4-oxo-4,5-dihydro-thiazol-2-yl]-carbamic acid tert-butyl ester (50.0 mg, 0.12 mmol) (see Example 26) in xylenes (2.0 mL) was heated to 150° C. with CEM microwave synthesizer for 1 h, cooled to r.t. and diluted with xylenes. The solid was collected by filtration and washed with acetone and ether to give 2-amino-5-(8-isopropoxy-[1,5]naphthyridin-2-ylmethylene)-thiazol-4-one as a light brown solid (27.3 mg, 72.0%). HR-ES (+) m/e calcd for $C_{15}H_{14}N_4O_2S$ (M+H)$^+$ 315.0910. found 315.0911.

Example 28

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 μM. This demonstrates that all of these compounds were active to inhibit CDK1/Cyclin B.

Kinase Assays

To determine inhibition of CDK1 activity, either FlashPlate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5×final concentration. Reactions were initiated by immediate addition of 40 μl reaction mix (25 mM HEPES, 20 mM $MgCl_2$, 0.002% Tween 20, 2 mM DTT, 1 μM ATP, 3.3 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.). The percent inhibition of Rb phosphorylation, which is a measure of the inhibition of CDK1 activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The $IC_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM $MgCl_2$, 1.5 mM DTT, and 162 µM ATP) with DMSO concentration at 15%. The CDK1/Cyclin B enzyme was diluted in kinase assay buffer 2 (25 mM HEPES, pH 7.0, 8 mM $MgCl_2$, 0.003% Tween 20, 0.045% BSA, 1.5 mM DTT, and 0.675 µM Rb protein). To initiate the kinase reaction, 20 µL of compound solution was mixed with 40 µL of CDK1/Cyclin B solution in assay plates with final concentration of CDK1/Cyclin B and Rb at 0.1 µg/mL and 0.225 µM, respectively, and incubated at 37° C. for 30 min. 15 µL of anti-phospho-Rb (Ser 780) antibody (Cell Signaling Technology, Beverly, Mass.,) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject matter of this invention ranges from about 0.001 µM to about 5.000 µM, preferably from about 0.01 µM to about 0.8 µM. Specific data for some examples are as follows:

| Example | CDK1 Ki (µM) | CDK2 Ki (µM) | CDK4 Ki (µM) |
|---------|--------------|--------------|--------------|
| 1       | 0.008        | 0.018        | >10          |
| 2       | 0.150        | 0.610        | >10          |
| 3       | 0.078        | 0.351        | >10          |
| 4       | 0.047        | 0.554        | >10          |
| 17      | 0.539        | >10          | N/A          |

Example 29

Tablet Formulation

| Item | Ingredients | Mg/Tablet | | | | | |
|------|-------------|-----|-----|-----|-----|-----|-----|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:

Mix Items 1, 2 and 3 in a suitable mixer for 15 minutes.

Granulate the powder mix from Step 1 with 20% Povidone K30 Solution (Item 4).

Dry the granulation from Step 2 at 50° C.

Pass the granulation from Step 3 through a suitable milling equipment.

Add the Item 5 to the milled granulation Step 4 and mix for 3 minutes.

Compress the granulation from Step 5 on a suitable press.

Example 30

Capsule Formulation

| Item | Ingredients | mg/Capsule | | | | |
|------|-------------|-----|-----|-----|-----|-----|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:

Mix Items 1, 2 and 3 in a suitable mixer for 15 minutes.

Add Items 4 & 5 and mix for 3 minutes.

Fill into a suitable capsule.

Example 31

Injection Solution/Emulsion Preparation

| Item | Ingredient | mg/mL |
|------|------------|-------|
| 1 | Compound A * | 1 mg |
| 2 | PEG 400 | 10-50 mg |
| 3 | Lecithin | 20-50 mg |
| 4 | Soy Oil | 1-5 mg |
| 5 | Glycerol | 8-12 mg |
| 6 | Water q.s. | 1 mL |

Compound A represents a compound of the invention.

Manufacturing Procedure:

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 µm filter and fill into vials.

Example 32

Injection Solution/Emulsion Preparation

| Item | Ingredient | mg/mL |
|------|------------|-------|
| 1 | Compound A * | 1 mg |
| 2 | Glycofurol | 10-50 mg |
| 3 | Lecithin | 20-50 mg |
| 4 | Soy Oil | 1-5 mg |
| 5 | Glycerol | 8-12 mg |
| 6 | Water | q.s. 1 mL |

Compound A represents a compound of the invention.

Manufacturing Procedure:

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

The invention claimed is:

1. A compound of the formula:

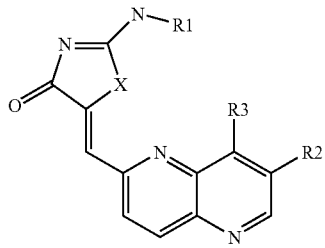

I wherein
X is —S— or —NH—;
$R^1$ is selected from the group consisting of
a) hydrogen,
b) lower alkyl that optionally may be substituted by
(1) aryl that optionally may be substituted by lower alkyl, OH, lower alkoxy, halogen, or perfluoro-lower alkyl,
(2) heteroaromatic that optionally may be substituted by lower alkyl, =O, and —NH, or
(3) heterocyclo lower alkyl,
c) cyclo lower alkyl that optionally may be substituted by aryl,
d) lower alkoxy-lower alkyl, e)

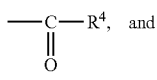

f)

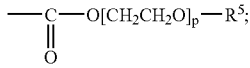

$R^2$ is selected from the group consisting of
a) cyano,
b) hydrogen,
c) $CONR^6R^7$,
d) $CO_2R^8$, and
e) lower alkyl optionally substituted by
(1) $OR^9$,
(2) cyano, or
(3) $NR^6R^7$;
$R^3$ selected from the group consisting of
a) O-lower alkyl,
b) S-lower alkyl,
c) hydrogen,
d) lower alkyl,
e) cyclo lower alkyl,
f) alkene,
g) alkylene,
h) $NR^6R^7$,
i) $COOR^8$, and
j) $CONR^6R^7$,
wherein, in each instance, lower alkyl, cyclo lower alkyl, lower alkene and lower alkylene may optionally be substituted by
(1) $OR^9$,
(2) cyano, and
(3) $NR^6R^7$,
$R^4$ is selected from the group consisting of
a) hydrogen,
b) lower alkyl,
c) O-lower alkyl,
d) cyclo lower alkyl containing from 3 to 6 carbon atoms, and e)

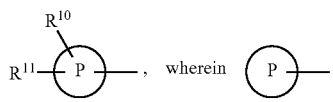

is selected from (1) an aryl ring, (2) a heterocyclo lower alkyl ring and (3) heteroaromatic ring;
$R^5$ is selected from the group consisting of hydrogen and lower alkyl;
$R^6$ and $R^7$ are each independently selected from the group consisting of
a) hydrogen,
b) lower alkyl which optionally may be substituted by
(1) $OR^9$,
(2) halogen,
(3) cyano, and
(4) $NR^{12}NR^{13}$, and
c) cyclo lower alkyl;
$R^8$ is selected from the group consisting of lower alkyl that optionally may be substituted by $OR^9$, cyano or $NR^6R^7$;
$R^9$ is selected from the group consisting of
a) hydrogen, and
b) lower alkyl that optionally may be substituted by
(1) $OR^{12}$,
(2) cyano, or
(3) $NR^6R^7$;
$R^{10}$ and $R^{11}$ are each independently selected from the group consisting of
a) hydroxy,
b) hydroxy-lower alkyl,
c) hydrogen,
d) lower alkyl,
e) halogen,
f) perfluro lower alkyl, and
g) lower alkoxy;
$R^{12}$ and $R^{13}$ are each independently selected from the group consisting of
a) hydrogen,
b) lower alkyl, and
c) cyclo lower alkyl; and
p is an integer from 0 to 6;
or a pharmaceutically acceptable salt thereof.

2. The compound of claim 1 wherein X is S.

3. The compound of claim 2 wherein $R^1$ is H.

4. The compound of claim 2 wherein $R^1$ is lower alkyl that optionally may be substituted by
(1) aryl that optionally may be substituted by lower alkyl, OH, lower alkoxy, halogen, or perfluoro-lower alkyl, (2) heteroaromatic that optionally may be substituted by lower alkyl, =O, and —NH, or (3) heterocyclo lower alkyl.

5. The compound of claim 2 wherein $R^1$ is cyclo lower alkyl that optionally may be substituted by aryl.

6. The compound of claim 2 wherein $R^1$ is lower alkoxy-lower alkyl.

7. The compound of claim 2 wherein $R^1$ is

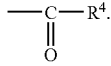

8. The compound of claim 7 wherein $R^4$ is lower alkyl.

9. The compound of claim 2 wherein $R^1$ is

10. The compound of claim 9 wherein $R^5$ is hydrogen and p is 1-2.

11. The compound of claim 2 wherein $R^2$ is cyano.

12. The compound of claim 2 wherein $R^2$ is hydrogen.

13. The compound of 2 wherein $R^2$ is $CONR^6R^7$.

14. The compound of claim 13 wherein $R^6$ and $R^7$ are each independently H, lower alkyl, or lower alkyl substituted by $OR^9$.

15. The compound of claim 14 wherein $R^9$ is hydrogen.

16. The compound of claim 2 wherein $R^2$ is $CO_2R^8$.

17. The compound of claim 16 wherein $R^8$ is lower alkyl which optionally may be substituted by $OR^9$.

18. The compound of claim 17 wherein $R^9$ is hydrogen or lower alkyl.

19. The compound of claim 2 wherein $R^2$ is lower alkyl optionally substituted by $OR^9$, cyano, or $NR^6R^7$.

20. The compound of claim 19 wherein $R^6$ is hydrogen or lower alkyl, $R^7$ is hydrogen or lower alkyl and $R^9$ is hydrogen or lower alkyl.

21. The compound of claim 2 wherein $R^3$ is O-lower alkyl wherein the lower alkyl optionally may be substituted by $OR^9$, wherein $R^9$ is H or lower alkyl.

22. The compound of claim 2 wherein $R^3$ is S-lower alkyl, wherein the lower alkyl optionally may be substituted by $OR^9$, wherein $R^9$ is H or lower alkyl.

23. The compound of claim 2 wherein $R^3$ is hydrogen.

24. The compound of claim 2 wherein $R^3$ is lower alkyl, wherein the lower alkyl optionally may be substituted by $OR^9$, wherein $R^9$ is as H or lower alkyl.

25. The compound of claim 2 wherein $R^3$ is cyclo lower alkyl, wherein the lower alkyl optionally may be substituted by $OR^9$.

26. The compound of claim 2 wherein $R^3$ is lower alkene, wherein the lower alkene optionally may be substituted $OR^9$, wherein $R^9$ is H or lower alkyl.

27. The compound of claim 2 wherein $R^3$ is lower alkylene, wherein the lower alkylene may be substituted by $OR^9$, wherein $R^9$ is H or lower alkyl.

28. The compound of claim 2 wherein $R^3$ is $NR^6R^7$, wherein $R^6$ and $R^7$ are each independently hydrogen or lower alkyl that optionally is substituted by $OR^9$, halogen or cyano, and wherein $R^9$ is H or lower alkyl.

29. The compound of claim 2 wherein $R^3$ is $COOR^8$ wherein $R^8$ is lower alkyl that is substituted by $OR^9$, wherein $R^9$ is H or lower alkyl.

30. The compound of claim 2 wherein $R^3$ is $CONR^6R^7$, wherein $R^6$ and $R^7$ are each independently hydrogen or lower alkyl that optionally is substituted by $OR^9$, halogen or cyano, and wherein $R^9$ is H or lower alkyl.

31. The compound of claim 4 wherein $R^1$ is lower alkyl substituted by aryl that is substituted by halogen and/or lower alkyl.

32. The compound of claim 4 wherein $R^1$ is lower alkyl substituted by heterocyclo lower alkyl.

33. The compound of claim 4 wherein $R^1$ is cyclo lower alkyl that optionally may be substituted by aryl.

34. The compound of claim 21 wherein $R^3$ is O-isopropyl.

35. The compound of claim 2 which is selected from the group:
 6-(2-Amino-4-oxo-4H-thiazol-5-ylidenemethyl)-4-isopropoxy-[1,5]naphthyridine-3-carbonitrile;
 6-[2-(2-Chloro-benzylamino)-5-oxo-3,5-dihydro-imidazol-4-ylidenemethyl]-4-isopropoxy-[1,5]naphthyridine-3-carbonitrile;
 4-Isopropoxy-6-[4-oxo-2-(2-phenyl-cyclopropylamino)-4H-thiazol-5-ylidenemethyl]-[1,5]naphthyridine-3-carbonitrile;
 4-Isopropoxy-6-{4-oxo-2-[(thiophen-2-ylmethyl)-amino]-4H-thiazol-5-ylidenemethyl}-[1,5]naphthyridine-3-carbonitrile;
 4-Isopropoxy-6-{2-[(3-methyl-thiophen-2-ylmethyl)-amino]-4-oxo-4H-thiazol-5-ylidenemethyl}-[1,5]naphthyridine-3-carbonitrile;
 6-[2-(2-Chloro-6-methyl-benzylamino)-4-oxo-4H-thiazol-5-ylidenemethyl]-4-isopropoxy-[1,5]naphthyridine-3-carbonitrile;
 6-{2-[2-(3-Fluoro-phenyl)-ethylamino]-4-oxo-4H-thiazol-5-ylidenemethyl}-4-isopropoxy-[1,5]naphthyridine-3-carbonitrile;
 6-[2-(2-Chloro-4-fluoro-benzylamino)-4-oxo-4H-thiazol-5-ylidenemethyl]-4-isopropoxy-[1,5]naphthyridine-3-carbonitrile; and
 6-{4-Oxo-2-[(thiophen-2-ylmethyl)-amino]-4H-thiazol-5-ylidenemethyl}-[1,5]naphthyridine-3-carbonitrile.

36. The compound of claim 2 which is selected from the group:
 6-[4-oxo-2-(2-phenyl-cyclopropylamino)-4H-thiazol-5-ylidenemethyl]-[1,5]naphthyridine-3-carbonitrile.
 6-{2-[(3-Methyl-thiophen-2-ylmethyl)-amino]-4-oxo-4H-thiazol-5-ylidenemethyl}-[1,5]naphthyridine-3-carbonitrile;
 6-(2-Amino-4-oxo-4H-thiazol-5-ylidenemethyl)-[1,5]naphthyridine-3-carbonitrile;
 6-{2-[2-(3-fluoro-phenyl)-ethylamino]-4-oxo-4H-thiazol-5-ylidenemethyl}-[1,5]naphthyridine-3-carbonitrile;
 6-[2-(2-Chloro-benzylamino)-5-oxo-3,5-dihydro-imidazol-4-ylidenemethyl]-[1,5]naphthyridine-3-carbonitrile;
 6-[2-(2-Chloro-6-methyl-benzylamino)-4-oxo-4H-thiazol-5-ylidenemethyl]-[1,5]naphthyridine-3-carbonitrile;
 6-[2-(2-Chloro-4-fluoro-benzylamino)-4-oxo-4H-thiazol-5-ylidenemethyl]-[1,5]naphthyridine-3-carbonitrile;
 6-[2-(3-Chloro-4-fluoro-benzylamino)-4-oxo-4H-thiazol-5-ylidenemethyl]-[1,5]naphthyridine-3-carbonitrile; and
 5-(8-Isopropoxy-[1,5]naphthyridin-2-ylmethylene)-2-(2-phenyl-cyclopropylamino)-thiazol-4-one.

37. The compound of claim 2 which is selected from the group consisting of:
 2-[2-(3-Fluoro-phenyl)-ethylamino]-5-(8-isopropoxy-[1,5]naphthyridin-2-ylmethylene)-thiazol-4-one;
 5-(8-Isopropoxy-[1,5]naphthyridin-2-ylmethylene)-2-[(thiophen-2-ylmethyl)-amino]-thiazol-4-one;

2-(2-Chloro-benzylamino)-5-(8-isopropoxy-[1,5]naphthyridin-2-ylmethylene)-thiazol-4-one;

2-(3-Chloro-4-fluoro-benzylamino)-5-(8-isopropoxy-[1,5]naphthyridin-2-ylmethylene)-thiazol-4-one;

2-(2-Chloro-4-fluoro-benzylamino)-5-(8-isopropoxy-[1,5]naphthyridin-2-ylmethylene)-thiazol-4-one;

[5-(8-Isopropoxy-[1,5]naphthyridin-2-ylmethylene)-4-oxo-4,5-dihydro-thiazol-2-yl]-carbamic acid tert-butyl ester; and 2-Amino-5-(8-isopropoxy-[1,5]naphthyridin-2-ylmethylene)-thiazol-4-one.

38. The compound of claim 1 wherein X is —NH—.

39. The compound of claim 38 which is selected from

6-[2-(2,4-Bis-trifluoromethyl-benzylamino)-5-oxo-3,5-dihydro-imidazol-4-ylidenemethyl]-4-isopropoxy-[1,5]naphthyridine-3-carbonitrile, and 4-Isopropoxy-6-[5-oxo-2-(2-trifluoromethyl-benzylamino)-3,5-dihydro-imidazol-4-ylidenemethyl]-[1,5]naphthyridine-3-carbonitrile.

40. A pharmaceutical composition comprising a therapeutically effective amount of a compound of claim 1, or a pharmaceutically acceptable salt thereof, and a pharmaceutically acceptable carrier or excipient.

* * * * *